US011304952B2

(12) United States Patent
Campbell et al.

(10) Patent No.: US 11,304,952 B2
(45) Date of Patent: Apr. 19, 2022

(54) COMBINATION THERAPY USING A CHEMOKINE RECEPTOR 2 (CCR2) ANTAGONIST AND A PD-1/PD-L1 INHIBITOR

(71) Applicant: CHEMOCENTRYX, INC., Mountain View, CA (US)

(72) Inventors: James J. Campbell, Mountain View, CA (US); Zhenhua Miao, Mountain View, CA (US); Thomas J. Schall, Mountain View, CA (US); Israel Charo, Mountain View, CA (US); Shijie Li, Los Altos, CA (US); Christine Marie Janson, El Cerrito, CA (US); Rajinder Singh, Belmont, CA (US); Karen Ebsworth, San Francisco, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 433 days.

(21) Appl. No.: 16/139,745

(22) Filed: Sep. 24, 2018

(65) Prior Publication Data
US 2019/0134049 A1 May 9, 2019

Related U.S. Application Data

(60) Provisional application No. 62/562,952, filed on Sep. 25, 2017.

(51) Int. Cl.
| A61K 31/536 | (2006.01) |
| A61P 35/00 | (2006.01) |
| A61K 31/165 | (2006.01) |
| A61K 31/357 | (2006.01) |
| A61K 45/06 | (2006.01) |

(52) U.S. Cl.
CPC .......... *A61K 31/536* (2013.01); *A61K 31/165* (2013.01); *A61K 31/357* (2013.01); *A61K 45/06* (2013.01); *A61P 35/00* (2018.01)

(58) Field of Classification Search
CPC .. A61K 31/536; A61K 31/165; A61K 31/357; A61K 45/06; A61P 35/00
See application file for complete search history.

(56) References Cited

U.S. PATENT DOCUMENTS

| 6,949,546 | B2 | 9/2005 | Ko et al. |
| 8,168,757 | B2 | 5/2012 | Finnefrock et al. |
| 8,354,509 | B2 | 1/2013 | Carven et al. |
| 8,519,135 | B2 | 8/2013 | Chen |
| 8,546,408 | B2 | 10/2013 | Krasinski |
| 8,552,154 | B2 | 10/2013 | Freeman et al. |
| 8,629,133 | B2 | 1/2014 | Sugimoto |
| 8,741,295 | B2 | 6/2014 | Olive |
| 9,212,224 | B2 | 12/2015 | Cogswell et al. |
| 9,783,540 | B2 | 10/2017 | Fan et al. |
| 10,251,888 | B2 | 4/2019 | Bekker |
| 10,398,685 | B2 | 9/2019 | Bekker |
| 10,464,934 | B2 | 11/2019 | Fan et al. |
| 10,583,131 | B2 | 3/2020 | Bekker |
| 2006/0030582 | A1 | 2/2006 | DeMartino et al. |
| 2010/0144695 | A1 | 6/2010 | Zhang et al. |
| 2011/0312936 | A1 | 12/2011 | Lanter et al. |
| 2012/0004252 | A1 | 1/2012 | Ebel et al. |
| 2012/0040960 | A1 | 2/2012 | Zhang et al. |
| 2013/0123241 | A1 | 5/2013 | Ebel et al. |
| 2013/0344070 | A1 | 12/2013 | Huang et al. |
| 2014/0294898 | A1 | 10/2014 | Miller et al. |
| 2014/0341917 | A1 | 11/2014 | Nastri et al. |
| 2015/0203580 | A1 | 7/2015 | Papadopoulos et al. |
| 2015/0320859 | A1 | 11/2015 | Maecker et al. |
| 2016/0194307 | A1 | 7/2016 | Chupak et al. |
| 2016/0222060 | A1 | 8/2016 | Miller et al. |
| 2016/0340356 | A1 | 11/2016 | Fan et al. |
| 2017/0216301 | A1 | 8/2017 | Quinn et al. |
| 2017/0368043 | A1 | 12/2017 | Bekker |
| 2018/0086756 | A1 | 3/2018 | Fan et al. |
| 2019/0209573 | A1 | 7/2019 | Campbell et al. |
| 2019/0269664 | A1 | 9/2019 | Campbell et al. |
| 2019/0275015 | A1 | 9/2019 | Campbell et al. |
| 2020/0121688 | A1 | 4/2020 | Fan et al. |
| 2020/0179359 | A1 | 6/2020 | Bekker |
| 2020/0297708 | A1 | 9/2020 | Harrison et al. |
| 2021/0346361 | A1 | 11/2021 | Campbell et al. |

FOREIGN PATENT DOCUMENTS

| EA | 014960 B1 | 4/2011 |
| JP | 2013-526507 A | 6/2013 |
| JP | 2013-528657 A | 7/2013 |
| WO | 02/13824 A1 | 2/2002 |
| WO | 03/004487 A1 | 1/2003 |
| WO | 03/092586 A2 | 11/2003 |

(Continued)

OTHER PUBLICATIONS

Vogelstein et al. Nature Medicine (2004), vol. 10, pp. 789-799 (Year: 2004).*
Carter Expert Opinion on Therpaeuitc Patents (2013), vol. 23, pp. 549-568 (Year: 2013).*
Dolan et al. Cancer Control (2014), vol. 21, pp. 231-237 (Year: 2014).*
International Search Report and Written Opinion dated Jan. 23, 2019 corresponding to PCT/US2018/052408 filed Sep. 24, 2018; 19 pages.
Janson, Christine et al., "Abstract 5655: Inhibition of CCR2 potentiates checkpoint inhibitor immunotherapy in murine model of pancreatic cancer," (Jul. 2017); 77(13):: Abstract 5655; 2 pages.
Extended European Search Report corresponding to EP 16797279.3 (PCT/US2016033210) dated Oct. 26, 2018; 8 pages.
International Search Report and Written Opinion corresponding to PCT/US2016/033210 dated Aug. 16, 2016; 8 pages.

(Continued)

*Primary Examiner* — Taina D Matos Negron
(74) *Attorney, Agent, or Firm* — Mintz Levin Cohn Ferris Glovsky and Popeo PC

(57) ABSTRACT

The present disclosure is drawn to the combination therapy of a Chemokine Receptor 2 (CCR2) antagonist and a PD-1 and/or PD-L1 inhibitor in the treatment of cancer.

16 Claims, 14 Drawing Sheets

(56) References Cited

FOREIGN PATENT DOCUMENTS

| WO | 03/093231 A2 | 11/2003 |
|---|---|---|
| WO | 03/093266 A1 | 11/2003 |
| WO | 2004/041777 A2 | 5/2004 |
| WO | 2004/076411 A2 | 9/2004 |
| WO | 2004/082682 A1 | 9/2004 |
| WO | 2004/092124 A2 | 10/2004 |
| WO | 2004/094371 A2 | 11/2004 |
| WO | 2004/110376 A2 | 12/2004 |
| WO | 2005/044264 A1 | 5/2005 |
| WO | 2005/044795 A1 | 5/2005 |
| WO | 2005/067502 A2 | 7/2005 |
| WO | 2005/080371 A1 | 9/2005 |
| WO | 2005/115392 A2 | 12/2005 |
| WO | 2006/073592 A2 | 7/2006 |
| WO | 2006/074265 A2 | 7/2006 |
| WO | 2008/014381 A2 | 1/2008 |
| WO | 2008/014381 A3 | 1/2008 |
| WO | 2010/121011 A1 | 10/2010 |
| WO | 2011/100227 A1 | 8/2011 |
| WO | 2011/159852 A1 | 12/2011 |
| WO | 2013/152269 A1 | 10/2013 |
| WO | 2014/151634 A1 | 9/2014 |
| WO | 2015/026634 A1 | 2/2015 |
| WO | 2015/034820 A1 | 3/2015 |
| WO | 2015/160641 A2 | 10/2015 |
| WO | 2015/160641 A3 | 10/2015 |
| WO | 2016/039749 A1 | 3/2016 |
| WO | 2016/057624 A1 | 4/2016 |
| WO | 2016/077518 A1 | 5/2016 |
| WO | 2016/100285 A1 | 6/2016 |
| WO | 2016/100608 A1 | 6/2016 |
| WO | 2016/149351 A1 | 9/2016 |
| WO | 2016/187393 A1 | 11/2016 |
| WO | 2017/165125 A1 | 9/2017 |
| WO | 2018/005374 A1 | 1/2018 |
| WO | 2018/195283 A1 | 10/2018 |
| WO | 2019/144098 A1 | 7/2019 |

OTHER PUBLICATIONS

International Preliminary Report on Patentability corresponding to PCT/US2016/033210 dated Nov. 21, 2017; 6 pages.
International Search Report and Written Opinion dated Apr. 18, 2019 corresponding to PCT/US2019/012515 filed Jan. 7, 2019.
Ahmadzadeh, Mojgan et al., "Tumor antigen-specific CD8 T cells infiltrating the tumor express high levels of PD-1 and are functionally impaired," *Blood* (Aug. 20, 2009); 114(8):1537-1544.
Bonapace, L. et al., "Cessation of CCL2 inhibition accelerates breast cancer metastasis by promoting angiogenesis," *Nature* (Nov. 6, 2014); 515(7525):130-133; Abstract only.
Broggi, Achille et al., "Preparation of Single-cell Suspensions for Cytofluorimetric Analysis from Different Mouse Skin Regions," *Journal of Visualized Experiments* (Apr. 20, 2016); 110:e52589; 6 pages.
Butora, Gabor et al., "3-Amino-1-alkyl-cyclopentane carboxamides as small molecule antagonists of the human and murine CC chemokine receptor 2," *Bioorganic & Medicinal Chemistry Letters* (Apr. 16, 2007); 17:3636-3641.
Cannarile, Michael A. et al., "Colony-stimulating factor 1 receptor (CSF1R) inhibitors in cancer therapy," *Journal for ImmunoTherapy of Cancer* (Published online Jul. 18, 2017); 5:53; 13 pages.
Carter, Percy H. et al., "Advances in the Discovery of CC Chemokine Receptor 2 Antagonists," *Annual Reports in Medicinal Chemistry* (2007); 42:211-227 [ISSN 0065-7743; DOI 10.1016/S0065-7743(07)42014-0].
Chen, Lieping et al., "Anti-PD-1/PD-L1 therapy of human cancer: past, present, and future," *J Clin Invest.* (Sep. 1, 2015); 125(9):3384-3391.
Chen, Xuguang et al., "CCL2/CCR2 Regulates the Tumor Microenvironment in HER-2/neu-Driven Mammary Carcinomas in Mice," *PLOS One* (Nov. 7, 2016) DOI:10.1371/journal.pone. 01655595; 20 pages.

Cherney, Robert J. et al., "Discovery of Disubstituted Cyclohexanes as New Class of CC Chemokine Receptor 2 Antagonists," *J. Med. Chem.* (published on Web Jan. 31, 2008); 51(4):721-724.
Cheung, K.-John J. et al., "Acquired *TNFRSF14* Mutations in Follicular Lymphoma Are Associated with Worse Prognosis," *Molecular and Cellular Pathobiology* (Nov. 15, 2010); Cancer Res; 70(22):9166-9174.
Cohen, Ivan J. et al., "Impact of the Tumor Microenvironment on Tumor-Infiltrating Lymphocytes: Focus on Breast Cancer," *Breast Cancer: Basic and Clinical Research* (Accepted Aug. 14, 2017); 11:1-12.
De Zeeuw, D. et al., Abstract Only: "The effect of CCR2 inhibitor CCX140-B on residual albuminuria in patients with type 2 diabetes and nephropathy: a randomized trial," *Lancet Diabetes Endocrinol* (Sep. 2015; Epub Aug. 9, 2015); 3(9):687-696.
Franklin, Ruth A. et al., "The Cellular and Molecular Origin of Tumor-associated Macrophages," *Science* (May 23, 2014); 344(6186):921-925.
Fujimura, Taku et al., "Regulatory T Cells Stimulate B7-H1 Expression in Myeloid-Derived Suppressor Cells in *ret* Melanomas," *Journal of Investigative Dermatology* (2012; published online Dec. 22, 2011); 132:1239-1246.
Fujimura, Taku et al., "Tumor-Associated Macrophages: Therapeutic Targets for Skin Cancer," *Frontiers in Oncology* (Jan. 23, 2018); 8(3); 6 pages.
Gao, Zhongli et al., "Unraveling the Chemistry of Chemokine Receptor Ligands," *Chem. Rev.* (2003); 103:3733-3752.
Gong, Jiang-Hong et al., "An Antagonist of Monocyte Chemoattractant Protein 1 (MCP-1) Inhibits Arthritis in the MRL-*Ipr* Mouse Model," *J. Exp. Med.* (Jul. 7, 1997); 186(1):131-137.
Grivennikov, Sergei I., et al., "Immunity, Inflammation, and Cancer," *Cell* (Mar. 19, 2010); 140(6):883-899.
Hackam, Daniel G. et al., "Translation of Research Evidence from Animals to Humans," *JAMA* (Oct. 11, 2006); 296(14):1731-1732.
Hitchcock, Jessica R. et al., "Anti-CCL2: building a reservoir or opening the floodgates to metastasis?" *Breast Cancer Research* (Published online May 21, 2015); 17:68; 2 pages.
Hwang, S.T. et al., "Mycosis fungoides and Sézary syndrome," *Lancet* (Mar. 15, 2008); 371(9616):945-957.
Jordan, V.Craig, "Tamoxifen: A Most Unlikely Pioneering Medicine," *Nature Reviews: Drug Discovery* (Mar. 2003); 2:205-213.
Kang, Young Sun et al., "CCR2 antagonism improves insulin resistance, lipid metabolism, and diabetic nepropathy in type 2 diabetic mice," *Kidney International* (published online Aug. 4, 2010); 78:883-894.
Karihaloo, Anil et al., "Macrophages Promote Cyst Growth in Polycystic Kidney Disease," *J Am Soc Nephrol* (Oct. 2011; accepted May 12, 2011); 22(10):1809-1814.
Kitagawa, Kiyoki et al., "Blockade of CCR2 Ameliorates Progressive Fibrosis in Kidney," *American Journal of Pathology* (Jul. 2004; accepted Mar. 30, 2004); 165(1):237-245.
Kothandaraman, Shankaran et al., "Design, synthesis, and structure-activity relationship of novel CCR2 antagonists," *Bioorganic & Medicinal Chemistry Letters* (2009; accepted Dec. 10, 2008); 19:1830-1834.
Krejsgaard, Thorbjørn et al., "Malignant inflammation in cutaneous T-cell lymphoma—a hostile takeover," *Semin Immunopathol* (2017; published online Oct. 7, 2016); 39:269-282.
Lim, Jee Woong et al., "Synthesis and biological evaluation of 3-aminopyrrolidine derivatives as CC chemokine receptor 2 antagonsits," *Bioorganic & Medicinal Chemistry Letters* (2010; accepted Feb. 17, 2010); 20:2099-2102.
Lim, Su Yin et al., "Targeting the CCL2-CCR2 signaling axis in cancer metastasis," *Oncotarget* (Feb. 14, 2016); 7(19):28697-28710.
Miura, Kouichi et al., "Hepatic recruitment of macrophages promotes nonalcoholic steatohepatitis through CCR2," *Am J Physiol Gastrointest Liver Physiol* (Mar. 22, 2012) 302:G1310-G1321.
Miyagaki, T. et al., "Increased CCL18 expression in patients with cutaneous T-cell lymphoma: association with disease severity and prognosis," *Journal of the European Academy of Dermatology and Venereology*, (2013; Accepted Feb. 13, 2012); 27:e60-e67.

(56) References Cited

OTHER PUBLICATIONS

Moree, Wilna J. et al., "Potent antagonists of the CCR2b receptor. Part 3: SAR of the (R)-3-aminopyrrolidine series," *Bioorganic & Medicinal Chemistry Letters* (2008; accepted Feb. 7, 2008); 18:1869-1873.

Nywening, Timothy M., M.D. et al., "Phase 1b study targeting tumour associated macrophages with CCR2 inhibition plus FOLFIRINOX in locally advanced and borderline resectable pancreatic cancer," *Lancet Oncol.* May 2016); 17(5):651-662.

Papadopoulos, Kyriakos P. et al., "First-in-Human Study of AMG 820, a Monoclonal Anti-Colony-Stimulating Factor 1 Receptor Antibody, in Patients with Advanced Solid Tumors," *Clin Cancer Res* (Oct. 1, 2017); 23(19):5703-5710.

Pasternak, Alexander et al., "Discovery of a Potent and Orally Bioavailable CCR2 and CCR5 Dual Antagonist," *ACS Med. Chem. Lett.* (2010; accepted Dec. 14, 2009); 1:14-18.

Pasternak, Alexander et al., "Potent heteroarylpiperidine and carboxyphenylpiperidine 1-alkyl-cyclopentane carboxamide CCR2 antagonists," *Bioorganic & Medicinal Chemistry Letters* (2008; accepted Dec. 11, 2007); 18:994-998.

Pasternak, Alexander et al., "Conformational studies of 3-amino-1-alkyl-cyclopentane carboxamide CCR2 antagonists leading to new spirocyclic antagonists," *Bioorganic & Medicinal Chemistry Letters* (2009; accepted Jan. 3, 2008); 18:1374-1377.

Pedersen, Martin B. et al., "High intratumoral macrophage content is an adverse prognostic feature in analplastic large cell lymphoma," *Histopathology* (Published online Mar. 4, 2014); 65:490-500.

Peranzoni, Elisa et al., "Macrophages impede CD8 T cells from reaching tumor cells and limit the efficacy of anti-PD-1 treatment," *PNAS* (Published online Apr. 9, 2018); 115(17):E4041-E4050.

Pienta, Kenneth J. et al., "Phase 2 study of carlumab (CNTO 888), a human monoclonal antibody against CC-chemokine ligand 2 (CCLS), in metastatic castration-resistant prostate cancer," *Invest New Drugs* (2013; published online Aug. 21, 2012); 31:760-768.

Press Release: ChemoCentryx's CCR2 Inhibitor CCX872 Shown to Reduce Liver Fibrosis in NASH Models, (Oct. 18, 2016); 4 pages.

PUBCHEM-'124' Create Date: Aug. 9, 2005; Date accessed Jul. 13, 2016; p. 3; compound; 13 pages.

Roblek, Marko et al. "Targeted delivery of CCR2 antagonist to activated pulmonary endothelium prevents metastasis," *J. Control Release* (Dec. 28, 2015); 220(Pt A):341-347.

Sandhu, Shahneen K. et al., "A first-in-human, first-in-class, phase I study of carlumab (CNTO 888), a human monoclonal antibody against CC-chemokine ligand 2 in patients with solid tumors," *Cancer Chemother Pharmacol* (Published online Feb. 6, 2013); 71:1041-1050.

Sanford, Dominic et al., "Inflammatory Monocyte Mobilization Decreases Patient Survival in Pancreatic Cancer: A Role for Targeting the CCL2/CCR2 Anxis," *Clin Cancer Res* (Jul. 1, 2013); 19(13):3404-3414.

Stanley, E. Richard et al., "CSF-1 Receptor Signaling in Myeloid Cells," *Cold Spring Harb Perspect Biol* (2014); 4(6):a021857; 21 pages.

Sugaya, Makoto et al., "Association of the Nos. of CD163+ cells in lesional skin and serum levels of soluble CD163 with disease progression of cutaneous T cell lymphoma," *Journal of Dermatological Science* (Accepted Jul. 20, 2012); 68:45-51.

Tang, Xiaoqiang et al., "Anti-tumour strategies aiming to target tumour-associated macrophages," *Immunology* (Accepted Oct. 22, 2012); 138:93-104.

Trujillo, John I. et al., "Design and synthesis of novel CCR2 antagonists: Investigation of non-aryl/heteroaryl binding motifs," *Bioorganic & Medicinal Chemistry Letters* (2011; accepted Jan. 13, 2011); doi:10.1016/j.bmcl.2011.01.052.

Ueno, Takayuki et al., "Significance of Macrophage Chemoattractant Protein-1 in Macrophage Recruitment, Angiogenesis, and Survival in Human Breast Cancer," *Clinical Cancer Research* (Aug. 2000; accepted May 22, 2000); 6:3282-3289.

Vestergaard, Christian et al., "Expression of CCR2 on Monocytes and Macrophages in Chronically Inflamed Skin in Atopic Dermatitis and Psoriasis," *Acta derm Venereol* (2004; accepted Apr. 12, 2004); 84:353-358.

Vippagunta, Sudha R. et al., "Crystalline solids," *Advanced Drug Delivery Reviews* (2001; accepted Dec. 21, 2000); 48:3-26.

Wein, Lironne et al., "Clinical Validity and Utility of Tumor-Infiltrating Lymphocytes in Routine Clinical Practice for Breast Cancer Patients: Current and Future Directions," *Frontiers in Oncology* (Aug. 3, 2017); 7(156); 10 pages.

Wu, Xuesong et al., "Upregulation of Inflammatory Cytokines and Oncogenic Signal Pathways Preceding Tumor Formation in a Murine Model of T-Cell Lymphoma in Skin," *Journal of Investigative Dermatology* (Published online Apr. 14, 2011); 131:1727-1734.

Wu, Xuesong et al., "Depletion of M2-Like Tumor-Associated Macrophages Delays Cutaneous T-Cell Lymphoma Development In Vivo," *Journal of Investigative Dermatology* (Published online Jun. 5, 2014); 134:2814-2822.

Wu, Xuesong et al., "Cutaneous T-Cell Lymphoma: The Yin and Yang of Inflammation and Neoplasia," *The Journal of Investigative Dermatology Symposium* (Jul. 2015); 17:34-35.

Xue, Chu-Biao et al., "Discovery of INCB3284, a Potent, Selective, and Orally Bioavailable hCCR2 Antagonist," *ACS Med. Chem. Lett.* (2011; published Mar. 31, 2011); 2:450-454.

Xue, Chu-Biao et al., "Discovery of INCB8761/PF-4136309, a Potent, Selective, and Orally Bioavailable CCR2 Antagonist," *ACS Medicine Chemistry Letters* (Published Oct. 5, 2011); 2:913-918.

Yang, Li et al., "Tumor-associated macrophages, potential targets for cancer treatment," *Biomarker Research* (Published online Aug. 8, 2017); 5:25; 6 pages.

Yao, Min et al., "Continuous Delivery of Neutralizing Antibodies Elevate CCL2 Levels in Mice Bearing MCF10CA1d Breast Tumor Xenografts," *Translational Oncology* (Oct. 2017; accepted Jun. 15, 2017); 10(5):734-743.

Yao, Wenbo et al., "A Natural CCR2 Antagonist Relieves Tumor-associated Macrophage-mediated Immunosuppression to Produce a Therapeutic Effect for Liver Cancer," *EBioMedicine* (Available online Jul. 18, 2017); 22:58-67.

Zhang, Jian et al., "Targeting chemokine (C-C motif) ligand 2 (CCL2) as an example of translation of cancer molecular biology to the clinic," *Prog Mol Biol Transl Sci* (2010); 95:31-53. doi:10.1016/B978-0-12-385071-3.00003-4.

Zheng, Yi et al., "Structure of CC Chemokine Receptor 2 with Orthosteric and Allosteric Antagonists," *Nature* (Dec. 15, 2016); 540(7633):458-461.

Partial Supplementary European Search Report dated May 27, 2021 corresponding to EP Appl 18857688.8 filed Sep. 24, 2018; 19 pages.

Dörwald, F. Zaragoza, Side Reactions in Organic Synthesis: A Guide to Successful Synthesis Design, *Weinheim: WILEY-VCH Verlag GmBH & Co. KGaA*, © 2005, Preface; 6 pages.

Guzik, Katarzyna et al., "Small-Molecule Inhibitors of the Programmed Cell Death-1/Programmed Death-Ligand 1 (PD-1/PD-L1) Interaction via Transiently Induced Protein States and Dimerization of PD-L1," *Journal of Medicinal Chemistry* (Jun. 14, 2017) 69(13):5857-5867.

Jung, Heiyoun et al., "Abstract A107: Inhibition of CCR@ potentiates the checkpoint inhibitor immunotherapy in pancreatic cancer," *Cancer Immunology Research* (Nov. 2016) XP055804244 Retrieved from the Internet: URL:https://cancerimmunolres.aacrjournals.Org/content/4/11_ Supplement/A107; 4 pages.

Le, Dung et al., "Abstract CT124: A phase Ib/II study of BMS-813160, a CC chemokine receptor (CCR) 2/5 dual antagonist, in combination with chemotherapy or nivolumab in patients (pts) with advanced pancreatic or colorectal cancer," *Cancer Research* (Jul. 2018) XP55804393, Retrieved from the Internet URL:https://cancerres.aacrjournals.org/content/78/13_Supplement/CT124; 4 pages.

Norman, Peter, "A dual CCR2/CCR5 chemokine antagonist, BMS-813160?" *Expert Opinion on Therapeutic Patents* (Sep. 22, 2011) 21(12):1919-1924.

Steinberg, Shannon M. et al., "Myeloid Cells that Impair Immunotherapy Are Restored in Melanomas with Acquired Resistance to BRAF Inhibitors," *Cancer Research* (Feb. 15, 2017) 77(7):1599-1610.

U.S. Appl. No. 16/824,585, filed Mar. 2020, Harrison et al.

(56) References Cited

OTHER PUBLICATIONS

Wikipedia article Spartalizumab; https://en.wikipedia.org/wiki/Spartalizumab; CAS No. 1935694-88-4; accessed Jun. 29, 2020 (1 page).
Extended European Search Report dated Sep. 14, 2021 corresponding to EP Appl 18857688.8 filed Sep. 24, 2018; 19 pages.
Gopinath Adithya et al., IMMU-09. Disruption of the CCL2-CCR2 Axis Augments the Effects of Immune Checkpoint Inhibitors to Slow Progression of Gliomas. *Neuro-Oncology* Nov. 30, 2017, vol. 19, No. suppl_6, p. vi114 (Abstract; 1 page).

* cited by examiner

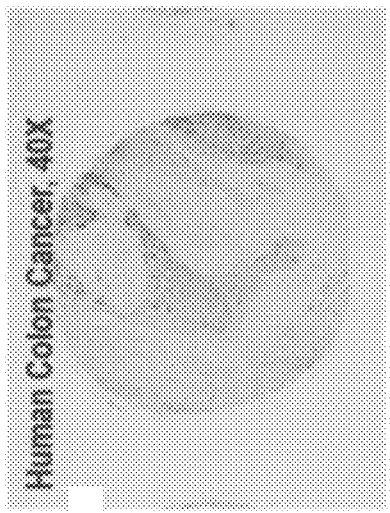
FIG 1A / FIG 1C / FIG 1E
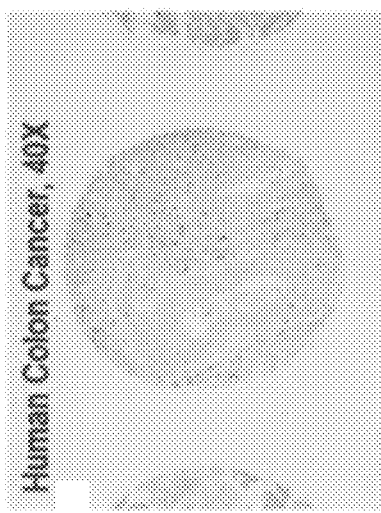
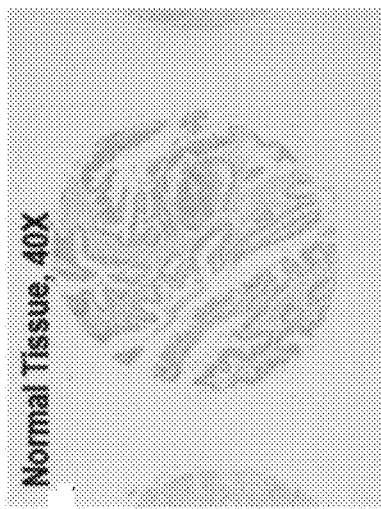
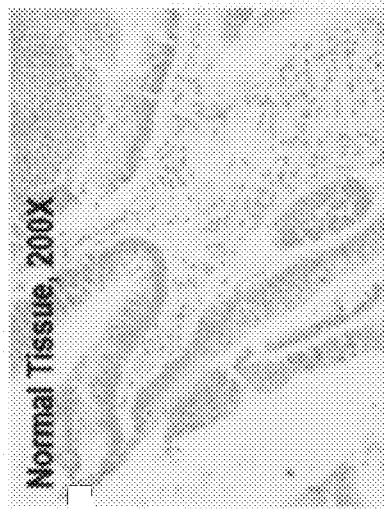
FIG 1B / FIG 1D / FIG 1F

COMBINATION THERAPY USING A CHEMOKINE RECEPTOR 2 (CCR2) ANTAGONIST AND A PD-1/PD-L1 INHIBITOR

CROSS-REFERENCES TO RELATED APPLICATIONS

This application claims the benefit of priority under 35 U.S.C § 119(e) to U.S. Provisional Application Ser. No. 62/562,952 filed Sep. 25, 2017, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

Cancerous tumors exploit numerous mechanisms to evade the body's natural cytotoxic immune response such that the tumors are tolerated by the immune system. These mechanisms include dysfunctional T-cell signaling, suppressive regulatory cells, and immune checkpoints that normally act to downregulate the intensity of adaptive immune responses and protect healthy tissues from collateral damage. For instance, tumors develop immune resistance, particularly to T cells that are specific to tumor antigens, by recruiting $CCR2^+$ myeloid-derived suppressor cells (MDSCs) and tumor-associated macrophages to the tumors and their surrounding microenvironment.

$CCR2^+$ MDSCs have immunosuppressive functions. MDSCs play a key role in a tumor's ability to suppress immune responses. Another key component to this suppression is the activation of immune checkpoints which, in turn, restricts T cell activation and infiltration into tumors. Immune checkpoints refer to inhibitory pathways of the immune system that are essential to maintaining self-tolerance and controlling immune responses in peripheral tissues to minimize collateral tissue damage.

Programmed Death-1 (PD-1) is one of numerous immune checkpoint receptors that are expressed by activated T cells and mediate immunosuppression. Ligands of PD-1 include Programmed Death Ligand-1 (PD-L1) and Programmed Death Ligand-2 (PD-L2) which are expressed on antigen-presenting cells as well as on many human cancer cells. PD-L1 and PD-L2 can downregulate T cell activation and cytokine secretion upon binding to PD-1.

It has been shown that PD-1/PD-L1 interaction inhibitors can mediate potent antitumor activity and are effective for treating some cancers. Despite these findings, there remains a need for an effective treatment for cancers such as solid tumor cancers.

BRIEF SUMMARY OF THE INVENTION

The present disclosure is drawn to the combination therapy of a Chemokine Receptor 2 (CCR2) antagonist and a PD-1 and/or PD-L1 inhibitor in the treatment of cancer.

In some embodiments, the CCR2 chemokine receptor antagonist has the formula I

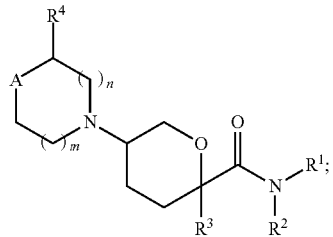

where each variable is described below.

In some embodiments, the CCR2 chemokine antagonist has the formula selected from the group consisting of

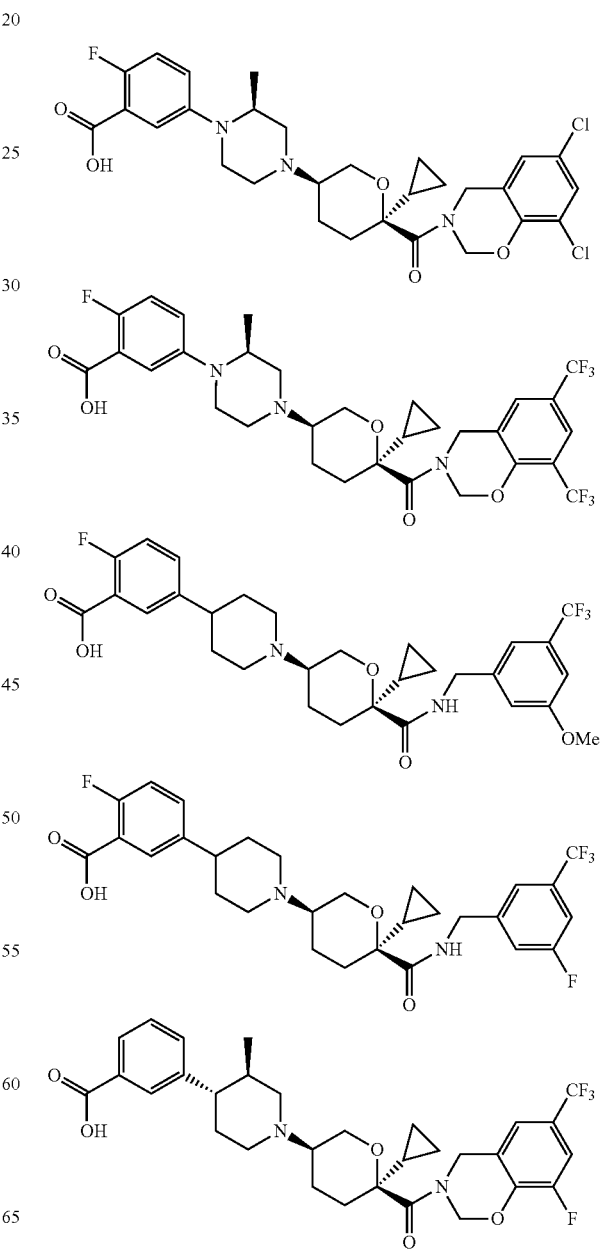

-continued

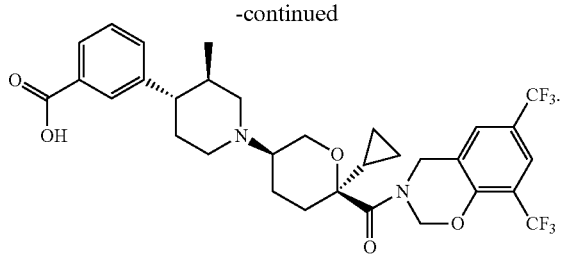

or a pharmaceutically acceptable salt thereof.

In some embodiments, the CCR2 antagonist has the formula (Compound 1)

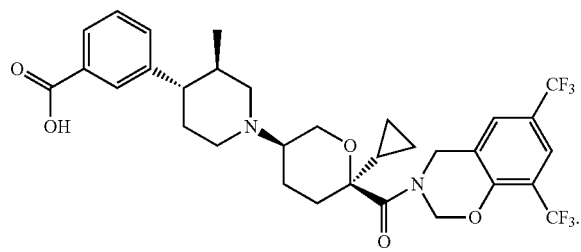

or a pharmaceutically acceptable salt thereof.

In some embodiments, the CCR2 antagonist has the formula (Compound 2)

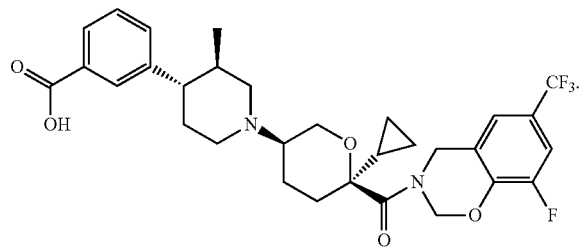

or a pharmaceutically acceptable salt thereof.

In some embodiments, the CCR2 antagonist has the formula (Compound 3)

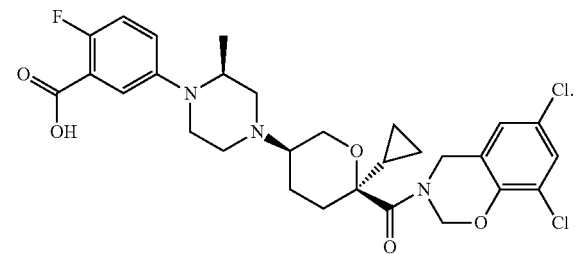

or a pharmaceutically acceptable salt thereof.

In some embodiments, the PD-1 and/or PD-L1 inhibitor is a PD-1 inhibitor.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, STI-1110, biosimilars thereof, biobetters thereof, and bioequivalents thereof.

In some embodiments, the PD-1 and/or PD-L1 inhibitor is a PD-L1 inhibitor.

In some embodiments, the PD-L1 inhibitor is selected from the group consisting of durvalumab, atezolizumab, avelumab, BMS-936559, ALN-PDL, TSR-042, KD-033, CA-170, STI-1014, KY-1003, biosimilars thereof, biobetters thereof, and bioequivalents thereof.

In some embodiments, the PD-1 and/or PD-L1 inhibitor is a compound of formula (II)

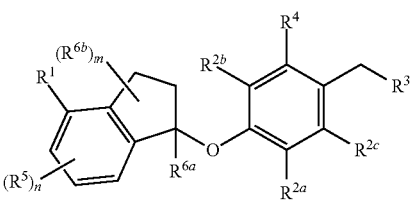

(II)

where each variable is described below.

In some embodiments, the cancer is a solid cancer. In some embodiments, the cancer is colorectal cancer. In some embodiments, the cancer is glioblastoma. In some embodiments, the cancer is pancreatic cancer.

Other objects, features, and advantages of the present invention will be apparent to one of skill in the art from the following detailed description and figures.

BRIEF DESCRIPTION OF THE DRAWINGS

FIGS. 1A-1F show immunohistochemistry analysis of normal and human tumor tissue using anti-hCCR2 Mab. Panels A and B show normal colon tissue at 40× and 200×, respectively. Panels C, D, E, and F, show human representative colon cancer tissue at the magnifications indicated. Specific CCR2 staining was observed on 78 malignant tumors (diagnosed Grade I-III) from colon carcinoma patients but not on normal control colon tissues.

DETAILED DESCRIPTION OF THE INVENTION

I. Abbreviation and Definitions

Figures 2A, 2B:
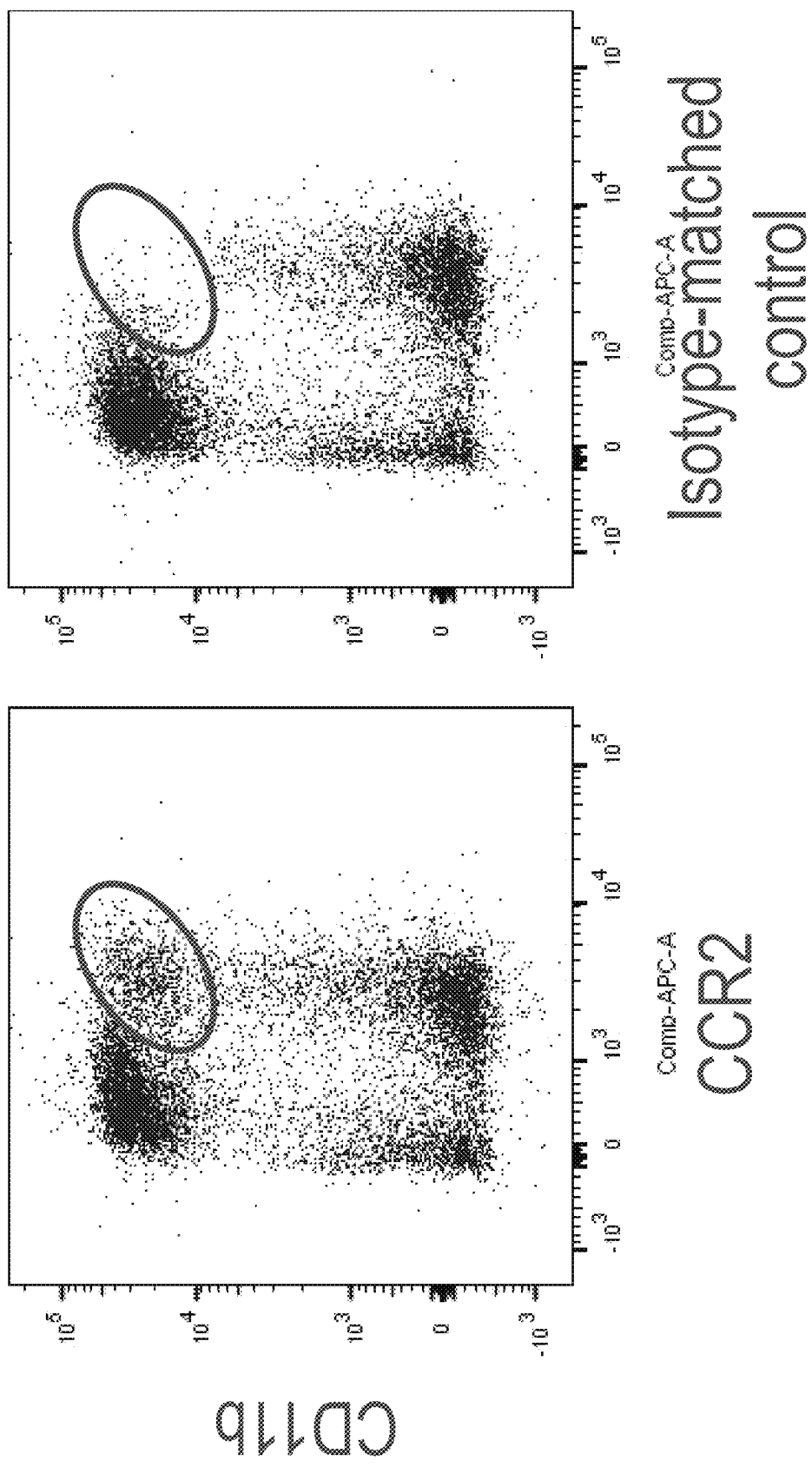
FIGS. 2A and 2B illustrate that CCR2 is expressed on a subset of CD11b+ Tumor-Infiltration Leukocytes within the CT27 Colorectal Cancer (CRC) Tumor Microenvironement. Gating on live CD45+ cells was employed. Panel A plots the data obtained using a CCR2 marker, while Panel B plots the data using an isotype-matched control. The circled region of each panel highlights the difference.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom. For terms such as cycloalkylalkyl and heterocycloalkylalkyl, it is meant that a cycloalkyl or a heterocycloalkyl group is attached through an alkyl or alkylene linker to the remainder of the molecule. For example, cyclobutylmethyl—is a cyclobutyl ring that is attached to a methylene linker to the remainder of the molecule.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "∼∼∼", that intersects a single, double or triple bond in any chemical structure depicted herein, represent the point attachment of the single, double, or triple bond to the remainder of the molecule.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group that is attached to the remainder of the molecule (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substitutent =O (e.g., —C(O)$CH_3$, —C(O)$CH_2CH_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S $(O)_2R''$, $-N_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-$(CH_2)_r$—B—, wherein A and B are independently —$CH_2$—, —O—, —NH—, —S—, —S(O)—, —$S(O)_2$—, —$S(O)_2NR'$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted $C_{1-6}$ alkyl.

As used herein, the term "heteroatom" is meant to include oxygen (O), nitrogen (N), sulfur (S) and silicon (Si).

For the compounds provided herein, a bond that is drawn from a substituent (typically an R group) to the center of an aromatic ring (e.g., benzene, pyridine, and the like) will be understood to refer to a bond providing a connection at any of the available vertices of the aromatic ring. In some embodiments, the depiction will also include connection at a ring which is fused to the aromatic ring. For example, a bond drawn to the center of the benzene portion of an indole, will indicate a bond to any available vertex of the six- or five-membered ring portions of the indole.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When compounds are provided herein with an identified stereochemistry (indicated as R or S, or with dashed or wedge bond designations), those compounds will be understood by one of skill in the art to be substantially free of other isomers (e.g., at least 80%, 90%, 95%, 98%, 99%, and up to 100% free of the other isomer).

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, glioblastoma and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The term "PD-1" or "PD-1 receptor" refers to the programmed death-1 protein, a T-cell co-inhibitor, also known as CD279. The amino acid sequence of the human full-length PD-1 protein is set forth, for example, in GenBank Accession Number NP_005009.2. PD-1 is a 288 amino acid protein with an extracellular N-terminal domain which is IgV-like, a transmembrane domain and an intracellular domain containing an immunoreceptor tyrosine-based inhibitory (ITIM) motif and an immunoreceptor tyrosine-based switch (ITSM) motif (Chattopadhyay et al., *Immunol Rev,* 2009, 229(1):356-386). The term "PD-1" includes recombinant PD-1 or a fragment thereof, or variants thereof. The PD-1 receptor has two ligands, PD-ligand-1 (PD-L1) and PD-ligand-2 (PD-L2).

The term "PD-L1" or "programmed death ligand 1" refers to a ligand of the PD-1 receptor also known as CD274 and B7H 1. The amino acid sequence of the human full-length PD-L1 protein is set forth, for example, in GenBank Accession Number NP_054862.1 PD-L1 is a 290 amino acid protein with an extracellular IgV-like domain, a transmembrane domain and a highly conserved intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, virally-infected cells and autoimmune tissue.

The programmed death 1 (PD-1/PD-L1) pathway acts as a checkpoint to limit T-cell-mediated immune responses. Both PD-1 ligands, PD-L1 and PD-L2, can engage the PD-1 receptor and induce PD-1 signaling and reversible inhibition of T-cell activation and proliferation. When PD-1 ligands on the surface or cancer cells or neighboring cells, these ligands bind to PD-1 receptor positive immune effector cells and utilize the PD-1 pathway to evade an immune response.

The term "immune checkpoint inhibitor" or "immune checkpoint blockade" refers to any agent, molecule, compound, chemical, protein, polypeptide, macromolecule, etc. that blocks or inhibits in a statistically, clinically, or biologically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD-1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55) and CGEN-15049. Illustrative immune checkpoint inhibitors include durvalumab (anti-PD-L1 antibody; MEDI4736), pembrolizumab (anti-PD-1 monoclonal antibody), nivolumab (anti-PD-1 antibody), pidilizumab (CT-011; humanized anti-PD-1 monoclonal antibody), AMP224 (recombinant B7-DC-Fc fusion protein), BMS-936559 (anti-PD-L1 antibody), atezolizumab (MPLDL3280A; human Fc-optimized anti-PD-L1 monoclonal antibody), avuelumab (MSB0010718C; human anti-PD-L1 antibody), ipilimumab (anti-CTLA-4 checkpoint inhibitor), tremelimumab (CTLA-4 blocking antibody), and anti-OX40.

The terms "CCR2 antagonist" and "CCR2 chemokine receptor antagonist" are used interchangeably and refer to a small molecule that antagonizes the interaction of the chemokine receptor CCR2 and any one of its ligands. Such a compound could inhibit processes normally triggered by the receptor ligand interaction.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

As used herein "mammal" is defined herein to include humans, other primates, cows, sheep, goats, horses, dogs, cats, rabbits, rats, mice and the like. The compounds, agents and compositions described herein are useful for treating a wide variety of cancers including solid tumor cancers.

The term "therapeutically effective amount" means the amount of the subject compound that will elicit the biological or medical response of a cell, tissue, system, or animal, such as a human, that is being sought by the researcher, veterinarian, medical doctor or other treatment provider.

II. General

The present disclosure is drawn to the surprising and unexpected finding that combination therapy using a CCR2 antagonist and a PD-1 and/or PD-L1 inhibitor significantly improves cancer treatment as compared to PD-1 and/or PD-L1 inhibition on its own.

III. Combination Therapy Using a CCR2 Antagonist and a PD-1 and/or PD-L1 Inhibitor Provided herein are methods, compositions, and kits that take advantage of the synergistic effect of CCR2 antagonists and PD-1 and/or PD-L1 inhibitors in treating cancer. A combination treatment that includes both a CCR2 antagonist and PD-1 and/or PD-L1 inhibitor is more effective at treating cancer compared to either compound/antibody alone.

In one aspect, provided herein are methods for treating cancer in a mammal. The method comprises administering to the subject in need thereof a therapeutically effective amount of a CCR2 chemokine receptor antagonist and a therapeutically effective amount of a PD-1 and/or PD-L1 inhibitor.

In some embodiments, the method comprises administering to the subject in need thereof a therapeutically effective amount of a CCR2 chemokine receptor antagonist and a therapeutically effective amount of a PD-1 inhibitor.

In some embodiments, the method comprises administering to the subject in need thereof a therapeutically effective amount of a CCR2 chemokine receptor antagonist and a therapeutically effective amount of a PD-L1 inhibitor.

In some embodiments, the CCR2 chemokine receptor antagonist is a compound of formula I of a subformulae thereof, below. In some embodiments, the CCR2 chemokine receptor antagonist is selected from the group consisting of

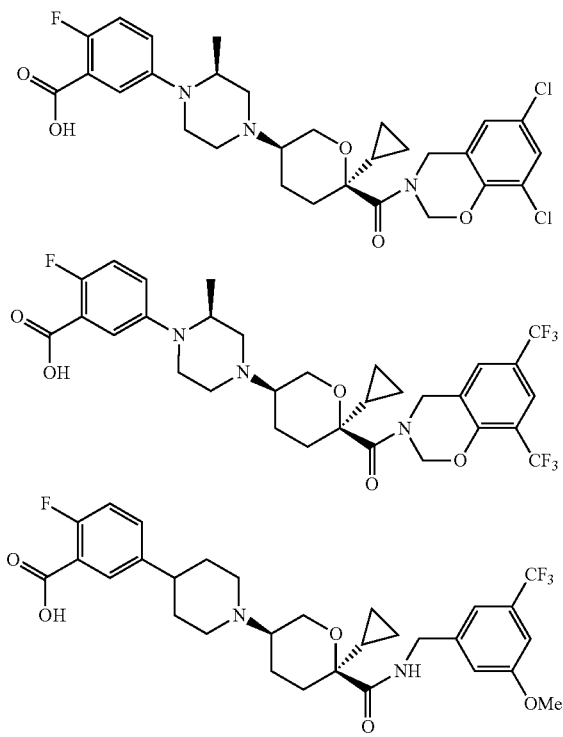

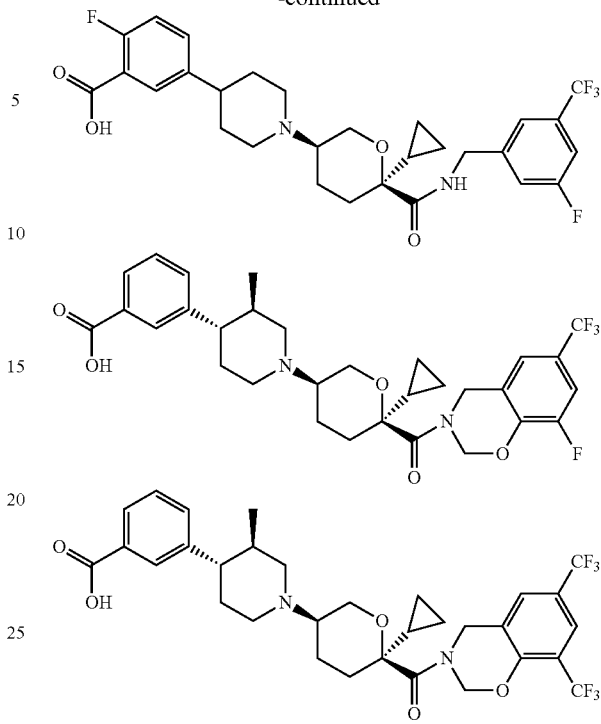

a pharmaceutically acceptable salt thereof.

In some embodiments, the CCR2 chemokine receptor antagonist is selected from the group consisting of AZ889, AZD2423, INCB-8761, MK-0812, BMS-813160, INCB-003284, PF-04634817, BMS-741672, Cenicriviroc, CCX-140.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, STI-1110, biosimilars thereof, biobetters thereof, and bioequivalents thereof.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, and STI-1110.

In some embodiments, the PD-1 inhibitor is RPM1-14.

In some embodiments, the PD-L1 inhibitor is selected from the group consisting of durvalumab, atezolizumab, avelumab, BMS-936559, ALN-PDL, TSR-042, KD-033, CA-170, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, CA-327, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-327, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, STI-1014, and KY-1003.

In some embodiments, the PD-1 and/or PD-L1 inhibitor is selected from the compounds disclosed in US2015291549, WO16039749, WO15034820, and US2014294898 (BRISTOL MYERS SQUIBB CO) which are thereby incorporated by reference.

In some embodiments, the PD-1 and/or PD-L1 inhibitor is selected from the compounds disclosed in WO14151634, WO15160641, WO16039749, WO16077518, WO16100608, WO16149351, WO2016057624, WO2016100285, US2016194307, US2016222060, and US2014294898 (BRISTOL MYERS SQUIBB CO) which are thereby incorporated by reference.

In some embodiments, the small molecule PD-1/PD-L1 inhibitor is selected from the compounds or pharmaceutical compositions disclosed in WO 2018/005374 filed by ChemoCentryx on Jun. 26, 2017. The contents of which is incorporated herein for all purposes.

In some embodiments, the CCR2 chemokine receptor antagonist and the PD-1 inhibitor or the PD-L1 inhibitor are formulated for concomitant administration.

In other embodiments, the CCR2 chemokine receptor antagonist and the PD-1 inhibitor or the PD-L1 inhibitor are formulated for sequential administration.

In some embodiments, the tumor can be a malignant or potentially malignant neoplasm or tissue mass of any size, and includes primary tumors and secondary neoplasms. A solid tumor can be an abnormal growth or mass of tissue that does not contain cysts or liquid areas.

In some embodiments, administering the compounds, agents and compositions of the present invention can decrease or reduce tumor burden, tumor load, tumor size, and/or the number of tumors in a subject. In some cases, the compounds, agents and compositions can prevent or minimize tumor metastasis. In other cases, the compounds, agents and compositions can promote or increase necrosis of the tumor.

In some embodiments, administering the compounds, agents and compositions of the present invention can lead to partial response or complete response (progression-free survival), delay progressive disease, and/or improve overall survival. In some cases, the compounds, agents and compositions can increase the durability of overall response to treatment, promote tumor regression, cancer regression, or disease stabilization, and/or provide a clinical benefit. In other cases, the compounds, agents and compositions can decrease the severity of at least one disease symptom, increase the frequency and duration of disease symptom-free periods, or prevent impairment or disability due to the cancer. In some instances, cancer development or cancer recurrence can be decreased.

Cancer generally includes any of various malignant neoplasms characterized by the proliferation of anaplastic cells that tend to invade surrounding tissue and metastasize to new body sites. Non-limiting examples of different types of cancer suitable for treatment using the compositions of the present invention include ovarian cancer, breast cancer, lung cancer (such as non-small-cell lung carcinoma), bladder cancer, thyroid cancer, liver cancer, pleural cancer, pancreatic cancer, cervical cancer, prostate cancer, testicular cancer, colon cancer, anal cancer, colorectal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, choriocarcinomas, head and neck cancers, bone cancer, osteogenic sarcomas, fibrosarcoma, Kaposi's sarcoma, epidermoid cancer, squamous cell cancer, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

Additional examples of cancers include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, squamous cell carcinoma, basal cell carcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In some embodiments, the cancer is lung cancer (e.g., non-small-cell lung carcinoma), melanoma, an epithelial cancer (e.g., prostate cancer, ovarian cancer, breast cancer), or a blood cancer (e.g., leukemia, lymphoma, multiple myeloma).

In some embodiments, the cancer is a solid cancer. In some embodiments, the cancer is colorectal cancer. In some embodiments, the cancer is glioblastoma. In some embodiments, the cancer is pancreatic cancer.

A. CCR2 Antagonists

In some embodiments, the CCR2 antagonists is a small molecule inhibitor of CCR2 having the formula (I):

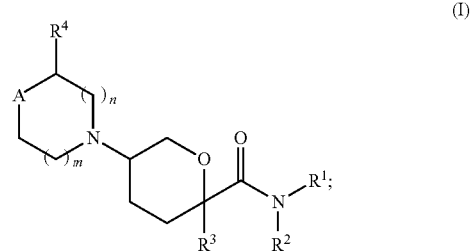

or a pharmaceutically acceptable salt, hydrate, stereoisomer or rotamer thereof, wherein A is $C(R^5)(R^6)$ or $N(R^5)$ the subscripts m and n are each independently integers of from 0 to 2, and m+n is ≤3;

$R^1$ is selected from the group consisting of aryl, aryl-$C_{1-4}$ alkyl, heteroaryl and heteroaryl-$C_{1-4}$ alkyl, wherein the heteroaryl portion has from 1-3 heteroatoms as ring members selected from N, O and S; and wherein said aryl and heteroaryl groups or portions are optionally substituted with from 1 to 5 $R^x$ substituents;

$R^2$ is selected from the group consisting of H, $C_{1-8}$ alkyl, $C_{3-8}$ cycloalkyl, $C_{3-8}$ cycloalkyl-$C_{1-4}$ alkyl, aryl, aryl-$C_{1-4}$ alkyl, heteroaryl and heteroaryl-$C_{1-4}$ alkyl, wherein the heteroaryl portion has from 1-3 heteroatoms as ring members selected from N, O and S; and wherein said aryl and heteroaryl groups or portions are optionally substituted with from 1 to 4 $R^x$ substituents;

or optionally, $R^1$ and $R^2$ are combined with the nitrogen atom to which each is attached to form a 6- to 11-membered monocyclic or fused bicyclic-heterocyclic or heteroaryl ring, wherein the —NR$^1$R$^2$ is optionally further substituted with from 1 to 4 R$^x$ substituents;

R$^3$ is selected from the group consisting of H, C$_{1-8}$ alkyl, C$_{3-8}$ cycloalkyl and C$_{3-8}$ cycloalkyl-C$_{1-4}$ alkyl, each of which is optionally substituted with from 1-3 R$^y$ substituents;

R$^4$ is selected from the group consisting of H, C$_{1-8}$ alkyl optionally substituted with 1 to 2 R$^y$, and —CO$_2$H:

R$^5$ is selected from the group consisting of C$_{1-8}$ alkyl, C$_{1-8}$ alkoxy, C$_{3-8}$ cycloalkyl, C$_{3-8}$ cycloalkyloxy, C$_{3-8}$ cycloalkyl-C$_{1-4}$ alkyl, C$_{1-8}$ alkylamino, di-C$_{1-8}$ alkylamino, aryl, aryloxy, arylamino, aryl-C$_{1-4}$ alkyl, heteroaryl, heteroaryloxy, heteroarylamino and heteroaryl-C$_{1-4}$ alkyl, each of which is optionally substituted with from 1 to 5 R$^z$ substituents;

R$^6$ is selected from the group consisting of H, F, OH, C$_{1-8}$ alkyl and C$_{1-8}$ alkoxy, wherein the C$_{1-8}$ alkyl and C$_{1-8}$ alkoxy groups are optionally substituted with from 1 to 3 R$^z$ substituents;

or optionally, R$^5$ and R$^6$ are joined to form a spirocyclic 5- or 6-membered cycloalkyl ring which is optionally unsaturated, and has a fused aryl group which is optionally substituted with from 1 to 4 R$^z$ substituents;

each R$^x$ is independently selected from the group consisting of
halogen, —CN, —R$^c$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^c$, —NR$^a$—C(O)NR$^a$R$^b$, —NR$^a$C(O)NR$^a$R$^b$, —NR$^a$R$^b$, —OR$^a$, —O—X$^1$—OR$^a$, —O—X$^1$—NR$^a$R$^b$, —O—X$^1$—CO$_2$R$^a$, —O—X$^1$—CONR$^a$R$^b$, —X$^1$—OR$^a$, —X$^1$—NR$^a$R$^b$, —X$^1$—CO$_2$R$^a$, —X$^1$—CONR$^a$R$^b$, —SF$_5$, —S(O)$_2$NR$^a$R$^b$, and 5- or 6-membered aryl or heteroaryl, wherein each X$^1$ is a C$_{1-4}$ alkylene; each R$^a$ and R$^b$ is independently selected from hydrogen, C$_{1-8}$ alkyl, and C$_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each R$^c$ is independently selected from the group consisting of C$_{1-8}$ alkyl, C$_{1-8}$ haloalkyl and C$_{3-6}$ cycloalkyl; and optionally when two R$^x$ substituents are on adjacent atoms, are combined to form a fused five or six-membered carbocyclic ring, and wherein the aryl or heteroaryl groups are optionally substituted with 1-3 members selected from halogen, hydroxyl, C$_{1-4}$ alkyl, C$_{1-4}$ alkoxy, C$_{1-4}$ haloalkyl, and C$_{1-4}$ haloalkoxy;

each R$^y$ is independently selected from the group consisting of halogen, —CN, —R$^f$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$C(O)NR$^d$R$^e$, —NR$^d$R$^e$, —OR$^d$, and —S(O)$_2$NR$^d$R$^e$; wherein each R$^d$ and R$^e$ is independently selected from hydrogen, C$_{1-8}$ alkyl, and C$_{1-8}$ haloalkyl, or when attached to the same nitrogen atom can be combined with the nitrogen atom to form a five or six-membered ring having from 0 to 2 additional heteroatoms as ring members selected from N, O or S; each R$^f$ is independently selected from the group consisting of C$_{1-8}$ alkyl, C$_{1-8}$ haloalkyl and C$_{3-6}$ cycloalkyl;

each R$^z$ is independently selected from the group consisting of halogen, —CN, —R$^i$, —CO$_2$R$^g$, —CONR$^g$R$^h$, —C(O)R$^g$, —OC(O)NR$^g$R$^h$, —NR$^h$C(O)R$^g$, —NR$^h$C(O)$_2$R$^i$, —NR$^g$C(O)NR$^g$R$^h$, —NR$^g$R$^h$, —OR$^g$, —S(O)$_2$NR$^g$R$^h$, —X$^1$—R$^j$, —X$^1$—NR$^g$R$^h$, —X$^1$—CONR$^g$R$^h$, —X$^1$—NR$^h$C(O)R$^g$, —NHR$^j$, —NHCH$_2$R$^j$, and tetrazole;

wherein each R$^g$ and R$^h$ is independently selected from hydrogen, C$_{1-8}$ alkyl, C$_{3-6}$ cycloalkyl and C$_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each R$^i$ is independently selected from the group consisting of C$_{1-8}$ alkyl, C$_{1-8}$ haloalkyl and C$_{3-6}$ cycloalkyl; and each R$^j$ is selected from the group consisting of C$_{3-6}$ cycloalkyl, pyrrolinyl, piperidinyl, morpholinyl, tetrahydrofuranyl, and tetrahydropyranyl.

It shall be understood that when R$^1$ and R$^2$ are combined with the nitrogen atom to which each is attached to form a 6- to 11-membered monocyclic or fused bicyclic-heterocyclic ring, the 6- to 11-membered monocyclic or fused bicyclic-heterocyclic ring encompasses monocyclic heterocyclic rings fused with an aryl or a heteroaryl ring.

In formula I, the substituent R$^3$ is, in one embodiment, selected from the group consisting of H, methyl, ethyl, propyl, isopropyl, buty, isobutyl, sec-butyl, cyclopropyl, cyclopropylmethyl, cyclobutyl and cyclobutylmethyl.

In the descriptions herein, one of skill in the art will understand that the wavy line intersecting a bond is meant to identify the point of attachment of a given substituent or group to the remainder of the molecule.

As noted above, the subscripts m and n are each integers selected from 0, 1 and 2, and m+n is ≤3. When the subscript is 0, one of skill in the are will understand that a cyclic structure with ring vertex A is intended, but that adjacent ring vertices on either side of the parentheses are joined by a bond. Accordingly, the present invention includes the structures wherein the ring having A as a vertex is meant to include:

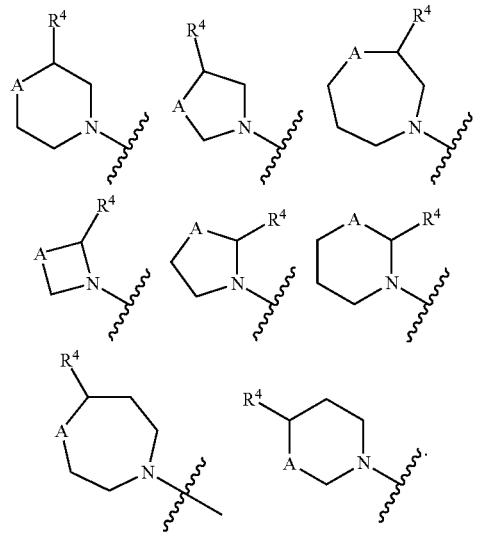

In one selected group of embodiments, m and n are both 0. In another selected group of embodiments, m and n are both 1. In yet another group of selected embodiments, m is 1 and n is 0. In still another group of embodiments, m is 1 and n is 2.

In still other selected embodiments, the ring having vertex A is represented by a formula selected from:

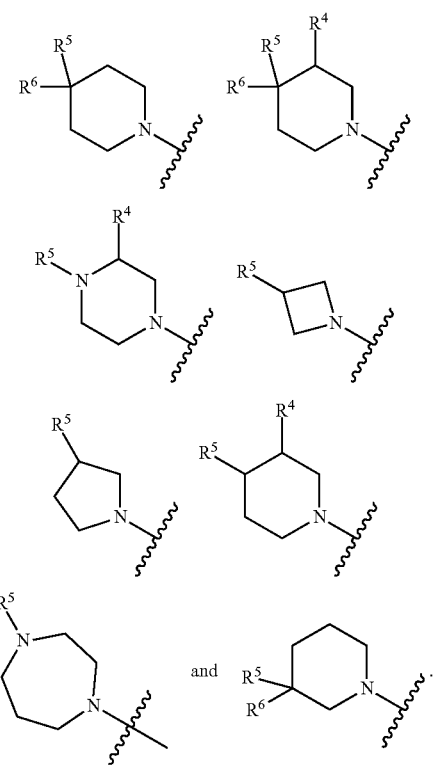

In one subgroup of embodiments, the compounds of formula (I) are represented by:

(Ia)

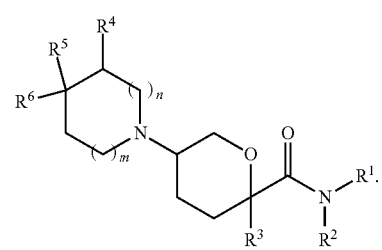

Within formula (Ia), a number of selected embodiments are provided as formulae Ia1, Ia2, Ia3, Ia4 and Ia5.

(Ia1)

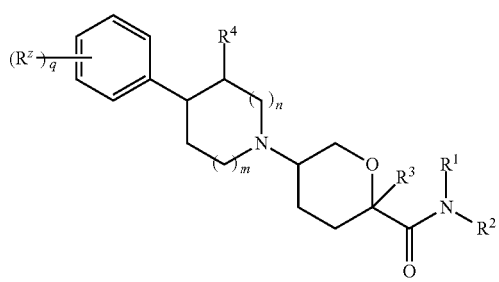

(Ia2)

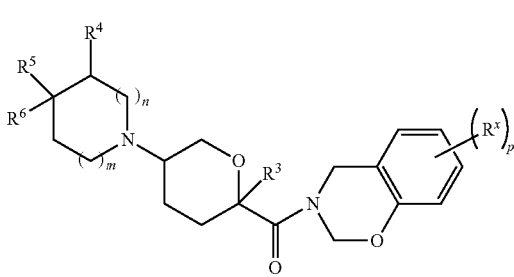

(Ia3)

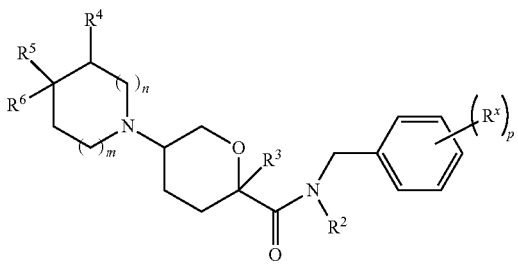

(Ia4)

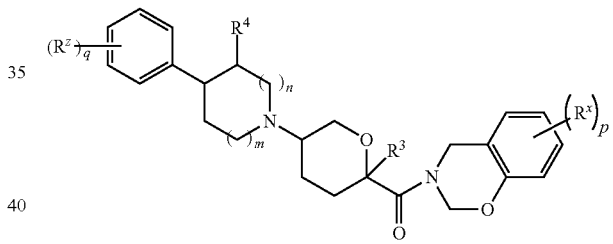

(Ia5)

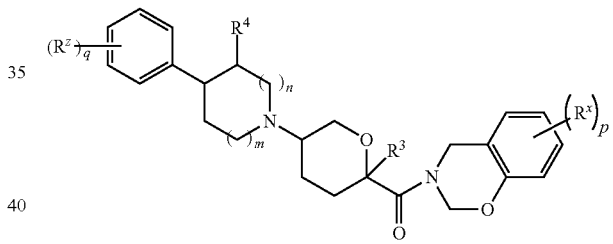

In each of formulae Ia, Ia1, Ia2, Ia3, Ia4 and Ia5, the noted substituents ($R^1$ through $R^6$, $R^x$ and $R^z$) and subscripts m and n have the meanings provided above with respect to formula I. The subscripts, p and q, have the following meanings: for Ia1, Ia4 and Ia5, the subscript q is an integer of from 0 to 5; for Ia2 and Ia4, the subscript p is an integer of from 0 to 4; and for Ia3 and Ia5, the subscript p is an integer of from 0 to 5.

In still other selected embodiments, the compounds provided herein are represented by formulae selected from:

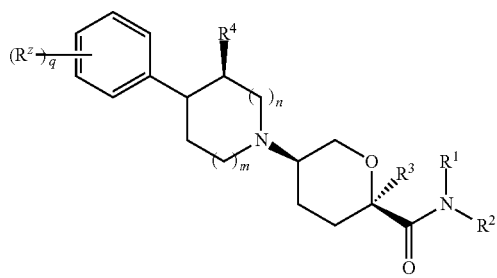

(Ia1')

(Ia2')

(Ia3')

(Ia4')

(Ia5')

wherein each compound is substantially free of other stereoisomers, and wherein the noted substituents ($R^1$ through $R^6$, $R^x$ and $R^z$) and subscripts m and n have the meanings provided above with respect to formula I. The subscripts, p and q, have the following meanings: for Ia1', Ia4' and Ia5', the subscript q is an integer of from 0 to 5; for Ia2' and Ia4', the subscript p is an integer of from 0 to 4; and for Ia3' and Ia5', the subscript p is an integer of from 0 to 5.

In another group of embodiments of formula I, A is $C(R^5)(R^6)$, wherein $R^5$ and $R^6$ are combined to form a ring. Selected embodiments are provided as follows:

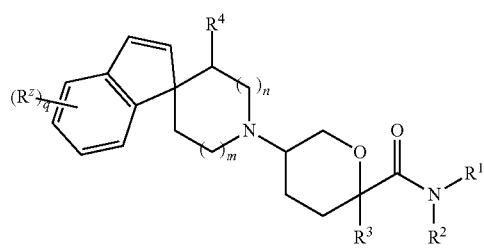

(Ib)

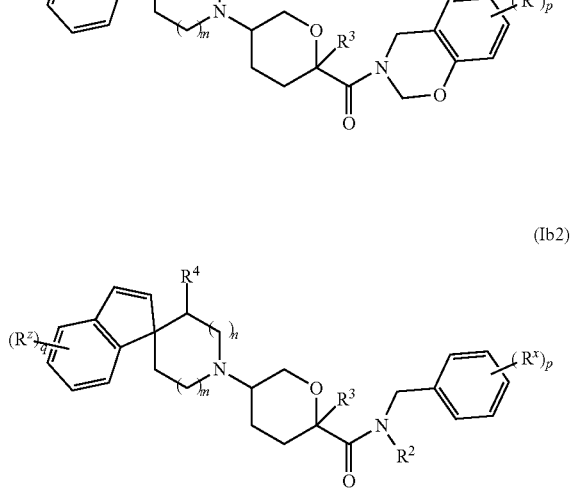

(Ib1)

(Ib2)

In each of formulae Ib, Ib1 and Ib2, the noted substituents ($R^1$ through $R^6$, $R^x$ and $R^z$) and subscripts m and n have the meanings provided above with respect to formula I. The subscripts, p and q, have the following meanings: for Ib, Ib1 and Ib2, the subscript q is an integer of from 0 to 5; for Ib1, the subscript p is an integer of from 0 to 4; and for Ib2, the subscript p is an integer of from 0 to 5.

In another group of embodiments of formula I, A is $NR^5$ (see formula Ic). Selected embodiments are provided as follows:

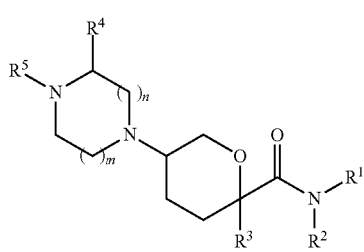

(Ic)

In still other selected embodiments, the compounds provided herein are represented by formulae selected from:

In each of formulae Ic, Ic, Ic2, Ic3, Ic4 and Ic5, the noted substituents (R¹ through R⁶, Rˣ and Rᶻ) and subscripts m and n have the meanings provided above with respect to formula I. The subscripts, p and q, have the following meanings: for Ic1, Ic4 and Ic5, the subscript q is an integer of from 0 to 5; for Ic2 and Ic4, the subscript p is an integer of from 0 to 4; and for Ic3 and Ic5, the subscript p is an integer of from 0 to 5.

wherein each compound is substantially free of other stereoisomers, and wherein the noted substituents (R¹ through R⁶, Rˣ and Rᶻ) and subscripts m and n have the meanings provided above with respect to formula L. The subscripts, p and q, have the following meanings: for Ic1', Ic4' and Ic5', the subscript q is an integer of from 0 to 5; for Ic2' and Ic4', the subscript p is an integer of from 0 to 4; and for Ic3' and Ic5', the subscript p is an integer of from 0 to 5.
Other selected embodiments, compounds are provided in each of I, Ia, Ia1, Ia1', Ib, Ic, Ic1 and Ic1', described above, wherein —N(R$^1$)(R$^2$) is selected from:
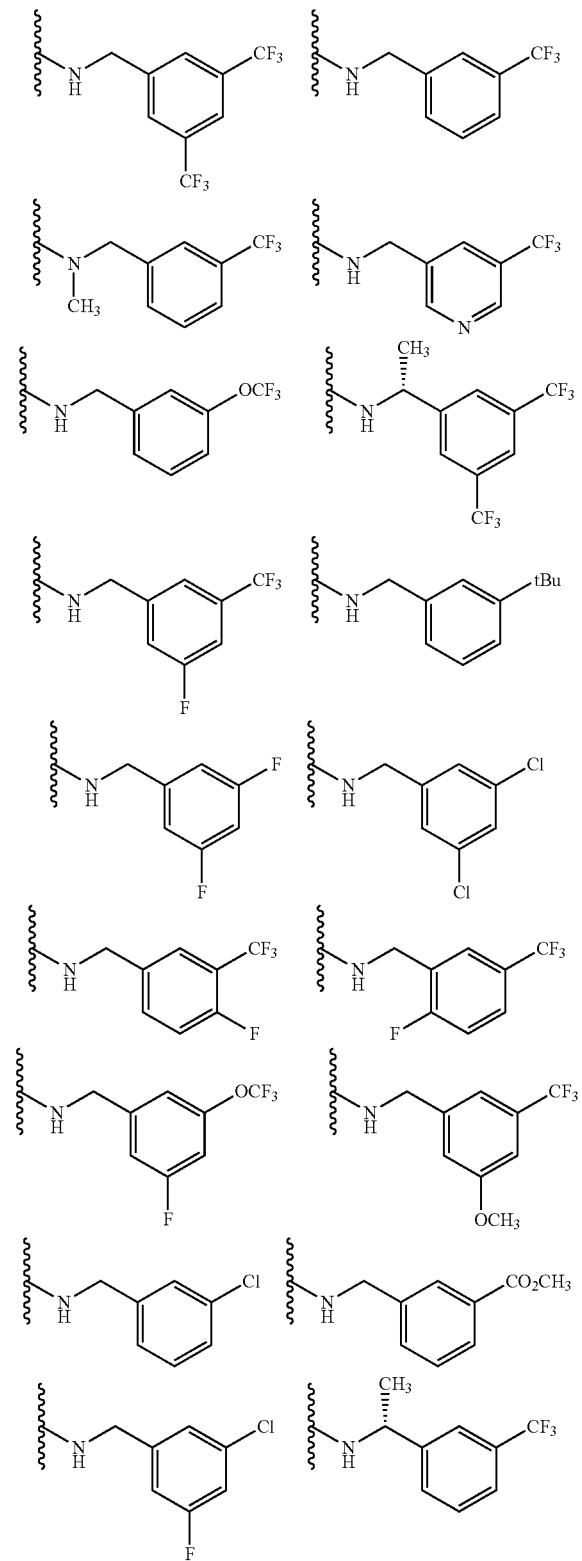
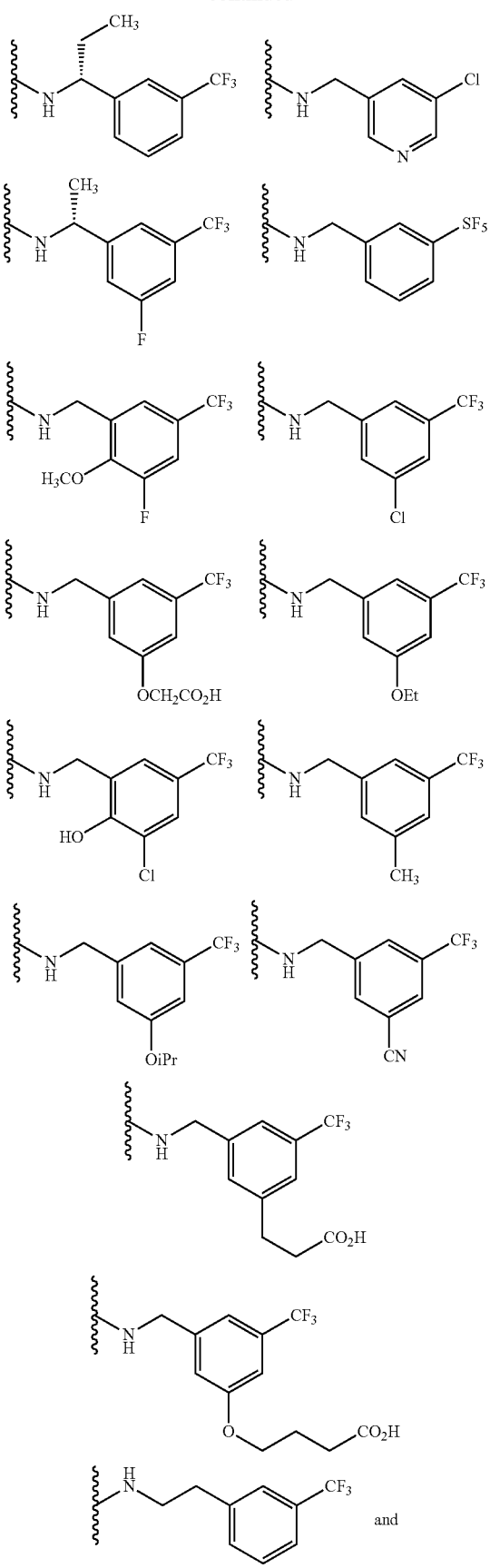

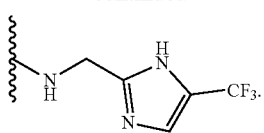
Still other selected embodiments, are provided in each of I, Ia, Ia1, Ia1', Ib, Ic, Ic1 and Ic1', described above, wherein —N(R¹)(R²) is selected from:
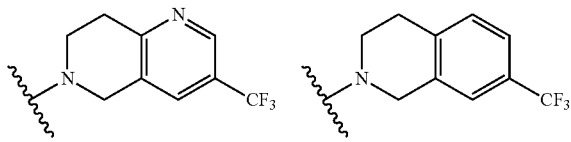
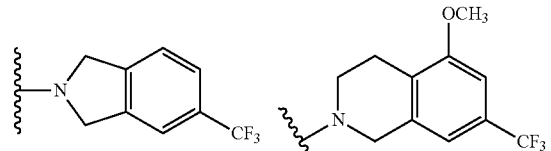
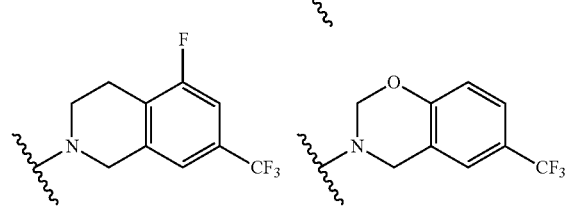
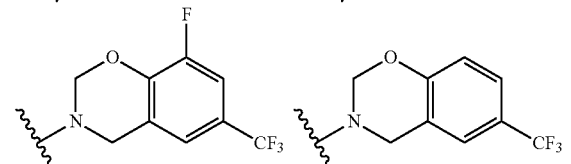
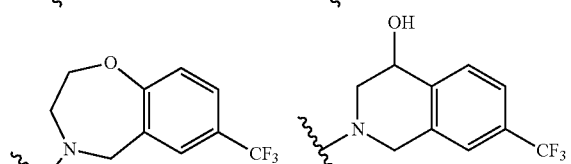
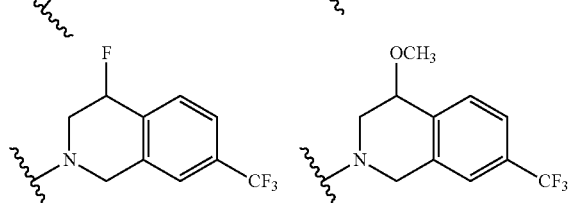
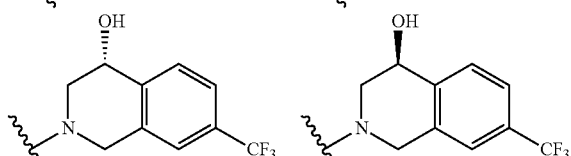
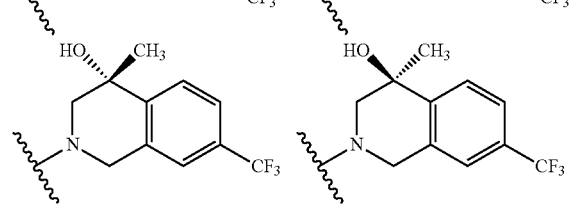
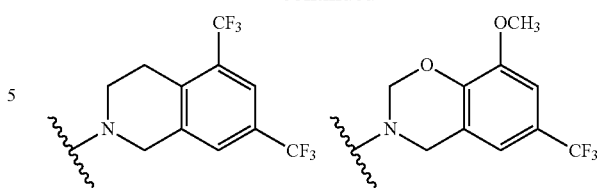
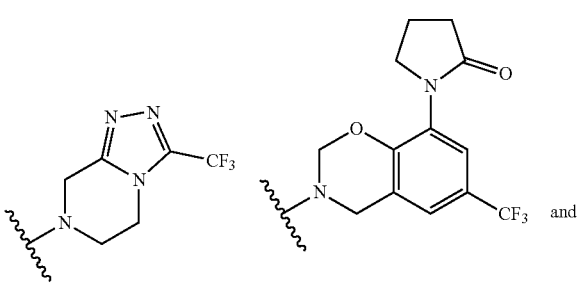
Yet other selected embodiments, are provided in each of I, Ia, Ia1, Ia1', Ib, Ic, Ic1 and Ic1', described above, wherein —N(R¹)(R²) is selected from:

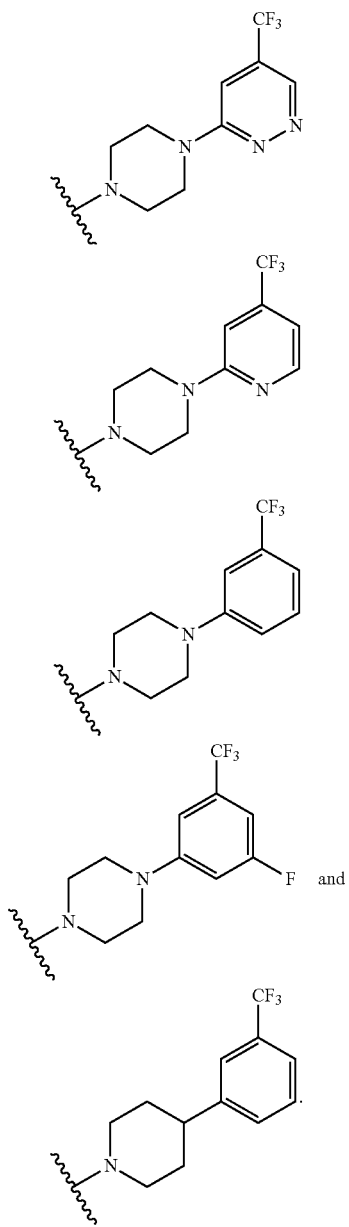
In some embodiments, compounds of formulae I, Ia, Ia2, Ia3, Ia2' and Ia3', are provided wherein A is $C(R^5)(R^6)$, or is shown in the formula as $C(R^5)(R^6)$, wherein $R^5$ is selected from aryl, aryloxy, arylamino, aryl-$C_{1-4}$ alkyl, heteroaryl, heteroaryloxy, heteroarylamino and heteroaryl-$C_{1-4}$ alkyl, wherein the aryl or heteroaryl groups or portions are selected from:
Group 1
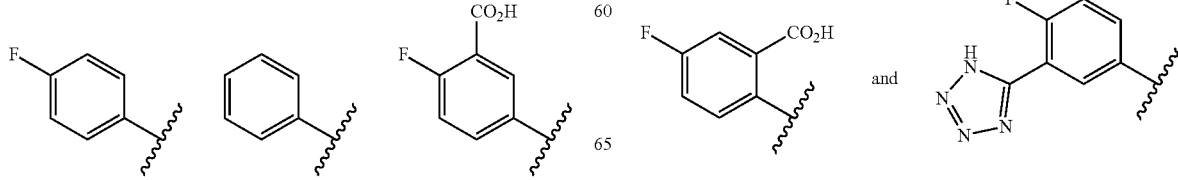
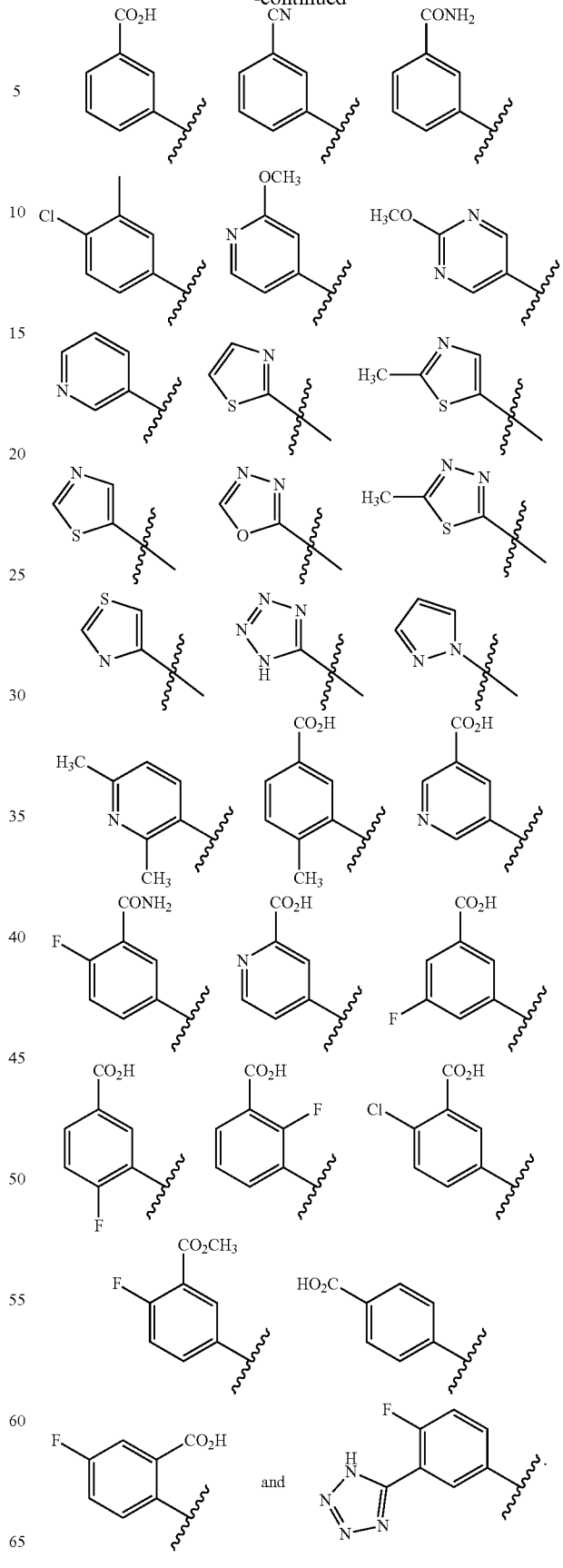

In certain selected embodiments, compounds of formulae I, Ia, Ia2, Ia3, Ia2' and Ia3' are provided wherein A is $C(R^5)(R^6)$, or is shown in the formula as $C(R^5)(R^6)$, wherein $R^5$ is selected from aryl, aryloxy, arylamino and aryl-$C_{1-4}$ alkyl, wherein the aryl group or portion is selected from:

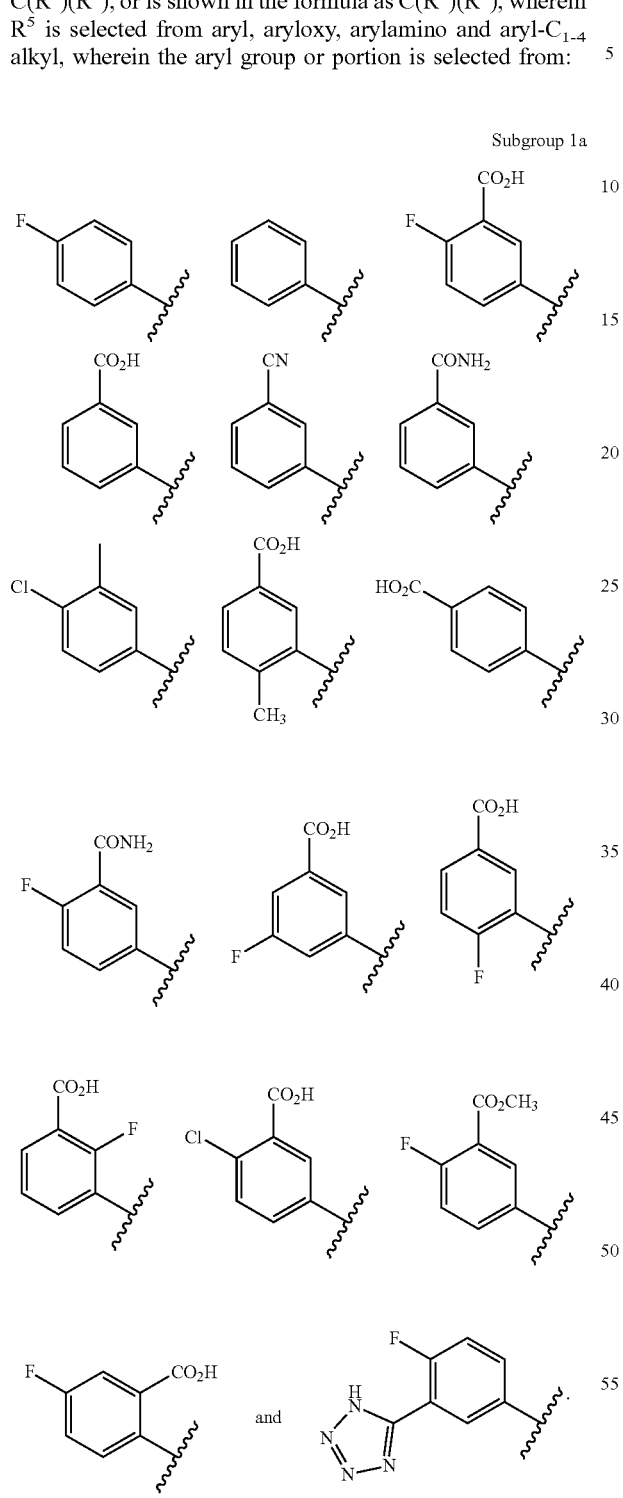

Subgroup 1a

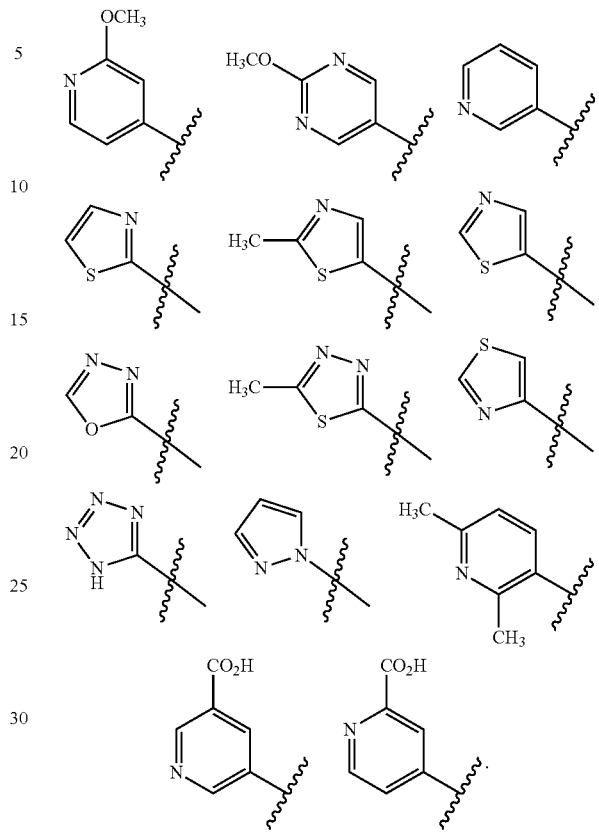

Subgroup 1b

In some embodiments, compounds of formulae I, Ic, Ic2, Ic3, Ic2' and Ic3', are provided wherein A is $N(R^5)$, or is shown in the formula as $N(R^5)$, wherein $R^5$ is selected from aryl, aryl-$C_{1-4}$ alkyl, heteroaryl and heteroaryl-$C_{1-4}$ alkyl, wherein the aryl or heteroaryl groups or portions are selected from Group 1 above. In certain selected embodiments, compounds of formulae I, Ic, Ic2, Ic3, Ic2' and Ic3', are provided wherein A is $N(R^5)$, or is shown in the formula as $N(R^5)$, wherein $R^5$ is selected from aryl and aryl-$C_{1-4}$ alkyl, wherein the aryl group or portion is selected from Subgroup 1a, above. In still other selected embodiments, compounds of formulae I, Ic, Ic2, Ic3, Ic2' and Ic3', are provided wherein A is $N(R^5)$, or is shown in the formula as $N(R^5)$, wherein $R^5$ is selected from heteroaryl and heteroaryl-$C_{1-4}$ alkyl, wherein the heteroaryl group or portion is selected from Subgroup 1b, above.

In some embodiments, the CCR2 antagonist has the formula selected from the group consisting of

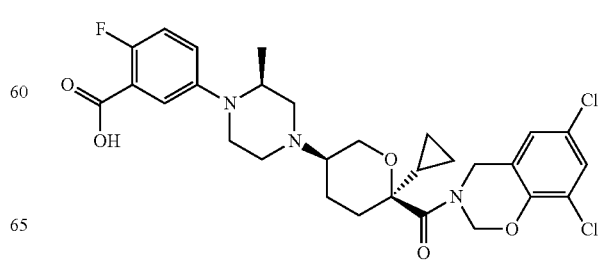

In still other selected embodiments, compounds of formulae I, Ia, Ia2, Ia3, Ia2' and Ia3', are provided wherein A is $C(R^5)(R^6)$, or is shown in the formula as $C(R^5)(R^6)$, wherein $R^5$ is selected from heteroaryl, heteroaryloxy, heteroarylamino and heteroaryl-$C_{1-4}$ alkyl, wherein the heteroaryl group or portion is selected from:

-continued

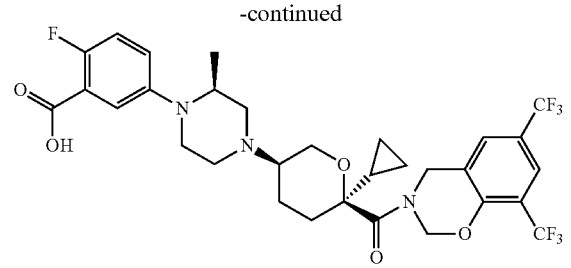

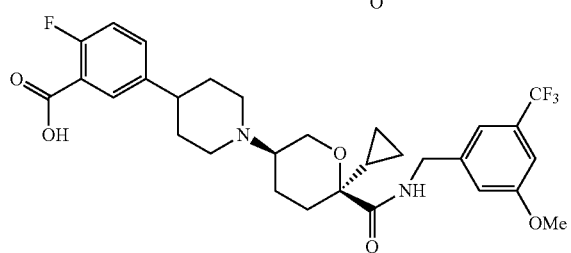

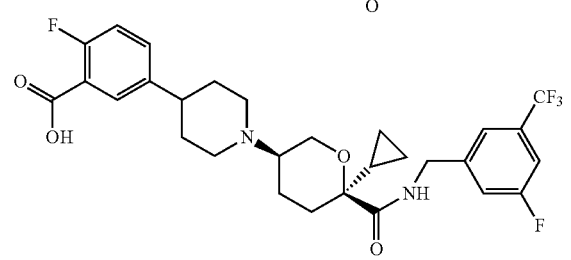

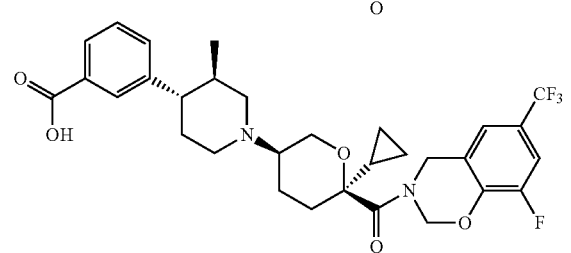

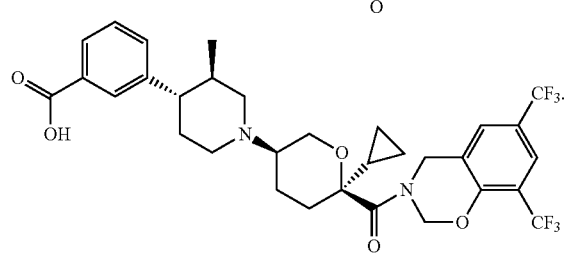

or a pharmaceutically acceptable salt thereof.

In some embodiments, the CCR2 antagonist has the formula (Compound 1)

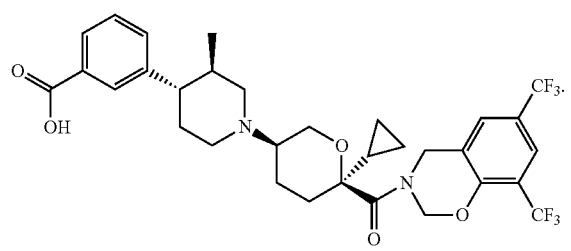

or a pharmaceutically acceptable salt thereof.

In some embodiments, the CCR2 antagonist has the formula (Compound 2)

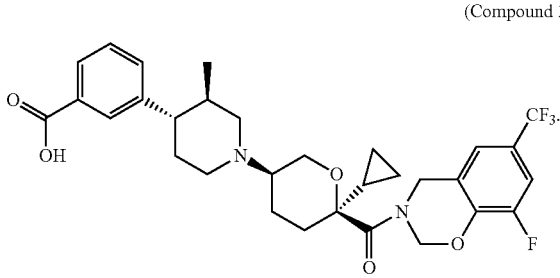 [SMILES: C[C@H]1CN([C@@H]2CC[C@@](C(=O)N3COc4c(F)cc(C(F)(F)F)cc4C3)(C3CC3)OC2)CC[C@@H]1c1cccc(C(=O)O)c1]

or a pharmaceutically acceptable salt thereof.

In some embodiments, the CCR2 antagonist has the formula (Compound 3)

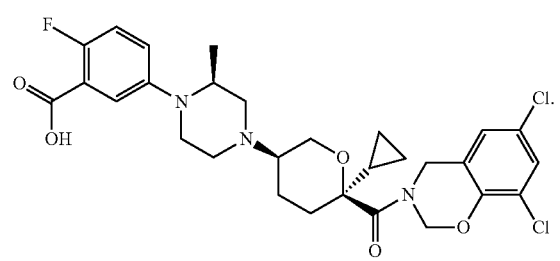

or a pharmaceutically acceptable salt thereof.

In some embodiments, the CCR2 antagonist is selected from the compounds or pharmaceutical compositions disclosed in US2016/0340356, stemming from application Ser. No. 15/158,713, filed on May 19, 2016 by ChemoCentryx. The contents of which is incorporated herein for all purposes.

In some embodiments, the CCR2 chemokine receptor antagonist is selected from the group consisting of AZ889, AZD2423, INCB-8761, MK-0812, BMS-813160, INCB-003284, PF-04634817, BMS-741672, Cenicriviroc, CCX-140.

B. PD-1 Inhibitors and PD-L1 Inhibitors

The methods, compositions, and kits provided herein include immune checkpoint inhibitors such as PD-1/PD-L1 pathway inhibitors (agents). The PD-1 and/or PD-L1 inhibitors of the present invention include small molecules and antibodies.

In some embodiments, a PD-L1 inhibitor can be durvalumab or atezolizumab or avelumab or BMS-936559 (MDX-1105) or ALN-PDL or TSR-042 or KD-033 or CA-170 or CA-327 or STI-1014 or MEDI-0680 or KY-1003.

In some embodiments, a PD-L1 inhibitor can be durvalumab or atezolizumab or avelumab or BMS-936559 (MDX-1105) or ALN-PDL or TSR-042 or KD-033 or CA-170 or STI-1014 or MEDI-0680 or KY-1003. Durvalumab (MEDI4736) is a human monoclonal antibody directed against PD-L1. Atrexolizumab (MPDL3280A) is a fully humanized, engineered IgG1 monoclonal antibody against PD-L1. Avelumab (MSB0010718C) is a fully humanized, engineered IgG1 monoclonal antibody against PD-L1. BMS-936559 (MDX-1105) is a fully human IgG4 monoclonal antibody against PD-L1. ALN-PDL is an inhibitory RNA (RNAi) targeting PD-L1. TSR-042 refers to an engineered chimeric antibody that is directed against the PD-1/PD-L1 pathway. KD-033 refers to a bifunctional anti-PD-L1/IL-15 fusion protein wherein the anti-PD-L1 antibody is linked at its tail to the cytokine IL-15 by the sushi domain of the IL-15 receptor. CA-170 refers to a small molecule antagonist of PD-L1 and VISTA. STI-1014 refers to an anti-PD-L1 antibody. KY-1003 is a monoclonal antibody against PD-L1. CA-327 refers to a small molecule antagonist of PD-L1 and TIM3.

In some embodiments, the PD-1 and/or PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, IBI-308, WBP-3155, JNJ-63723283, MEDI-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-L1/BCMA bispecific antibody (Immune Pharmaceuticals), PD-1/Ox40 targeting bispecific antibody (Immune Pharmaceuticals), BMS-936559, anti-PD-1/VEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics/NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

In some embodiments, a PD-1 inhibitor can be pembrolizumab or nivolumab or IBI-308 or mDX-400 or BGB-108 or MEDI-0680 or SHR-1210 or PF-06801591 or PDR-001 or GB-226 or STI-1110. Nivolumab (also known as OPDIVO™, MDX-1106, BMS-936558, and ONO-4538) is a human IgG4 monoclonal antibody against PD-1. Pembrolizumab (also known as KEYTRUDA®, lambrolizumab, and MK-34) is a humanized IgG4 kappa isotype monoclonal antibody against PD-1. IBI-308 refers to a monoclonal antibody directed to PD-1. mDX-400 refers to a mouse antibody against PD-1. BGB-108 is a humanized monoclonal antibody against PD-1. MEDI-0680 (AMP-514) is a humanized IgG4 monoclonal antibody against PD-1. SHR-1210 refers to a monoclonal antibody against PD-1. PF-06801591 is a monoclonal antibody against PD-1. PDR-001 refers to a monoclonal antibody against PD-1. GB-226 refers to a monoclonal antibody against PD-1. STI-1110 refers to a monoclonal antibody against PD-1.

In some embodiments, the PD-1 inhibitor is RPM1-14.

In some embodiments, the PD-1 inhibitor is an antibody selected from Nivolumab, Pembrolizumab, and Pidilizumab.

The anti-PD-1 antibodies, and antibody fragments described herein encompass proteins having amino acid sequences that vary from those of the described antibodies, but that retain the ability to bind PD-1.

In some embodiments, the anti-PD-1 antibodies include bispecific antibodies and antibody-like therapeutic proteins including DARTs®, DUOBODIES®, BITES®, XmAbs®, TandAbs®*, Fab derivatives, and the like that bind to PD-1.

The anti-PD-L1 antibodies and antibody fragments described herein encompass proteins having amino acid sequences that vary from those of the described antibodies, but that retain the ability to bind PD-L1. Such variant antibodies and fragments thereof can comprise one or more additions, deletions, or substitutions of amino acids when compared to the parent sequence, but exhibit biological activity that is essentially equivalent or essentially bioequivalent to that of the described antibodies.

In some embodiments, the anti-PD-L1 antibodies include bispecific antibodies and antibody-like therapeutic proteins including DARTs®, DUOBODIES®, BITES®, XmAbs®, TandAbs®, Fab derivatives, and the like that bind to PD-L1.

Non-limiting examples of additional PD-1/PD-L1 pathway inhibitors are described in, e.g., Chen and Han, *Jour Clin Invest*, 2015, 125(9):3384-3391, U.S. Pat. Nos. 8,168,757; 8,354,509; 8,552,154; 8,741,295; and 9,212,224; U.S. Patent App. Publ. Nos. 2014/0341917; 2015/0203580 and 2015/0320859; International Patent App. Publ. No. WO2015/026634.

A biological product, e.g., an antibody or a fragment thereof, is considered a biosimilar if, for example, the biological product is highly similar to an already FDA-approved biological product, known as the reference product. A biosimilar has no clinically meaningful differences in terms of safety and effectiveness from the reference product. A biosimilar can also have the same mechanism of action, route of administration, dosage form, and strength as its reference product.

Two biological products, e.g., antibodies or fragments thereof, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In some embodiments, two biological products (e.g., two antibodies or fragments thereof) are bioequivalent if there are no clinically meaningful differences in their safety, purity, or potency.

In other embodiments, two biological products (e.g., two antibodies or fragments thereof) are bioequivalent if a patient can be switched one or more times between the reference product and the biological product without an expected increase in the risk of adverse effects, including a clinically significant change in immunogenicity, or diminished effectiveness, as compared to continued therapy without such switching.

In yet other embodiments, two biological products (e.g., two antibodies or fragments thereof) are bioequivalent if they both act by a common mechanism of action for the condition of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Biobetter variants of the antibodies described herein may be based on an existing reference antibody specific for an target antigen, e.g., PD-1 or PD-L1, which has undergone changes such that, for example, it has a higher binding affinity to its target antigen and/or binds to a different epitope than the reference antibody, or has more desirable therapeutic efficacy, expression and/or biophysical characteristics.

In some embodiments, the PD-1 and/or PD-L1 inhibitor is a small molecule PD-1/PD-L1 inhibitor of having the formula:

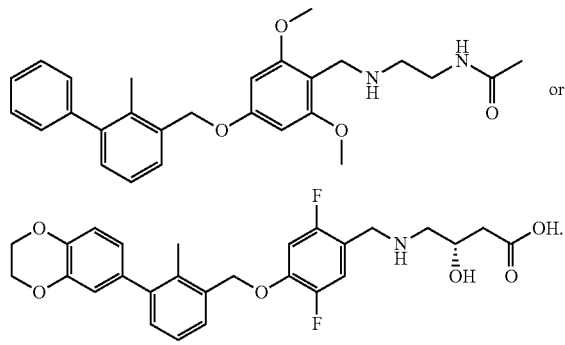

or

In some embodiments, the PD-1 and/or PD-L1 inhibitor is a small molecule PD-1/PD-L1 inhibitor having the formula (II)

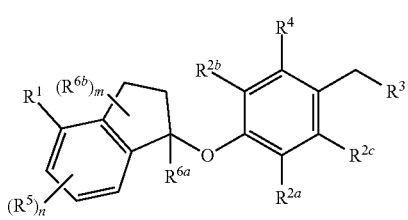

(II)

or a pharmaceutically acceptable salt thereof; wherein:
$R^1$ is selected from the group consisting of halogen, $C_{5-8}$ cycloalkyl, $C_{6-10}$ aryl and thienyl, wherein the $C_{6-10}$ aryl and thienyl are optionally substituted with 1 to 5 $R^x$ substituents;

each $R^x$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aR^b$, —$OR^a$, —O—$X^1$—$OR^a$, —O—$X^1$—$CO_2R^a$, —O—$X^1$—$CONR^aR^b$, —$X^1$—$OR^a$, —$X^1$—$NR^aR^b$, —$X^1$—$CO_2R^a$, —$X^1$—$CONR^aR^b$, —$SF_5$, and —$S(O)_2NR^aR^b$, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, wherein the five or six-membered ring is optionally substituted with oxo; each $R^c$ is independently selected from the group consisting of $C_{1-8}$ alkyl, $C_{2-8}$ alkenyl, $C_{2-8}$ alkynyl and $C_{1-8}$ haloalkyl; and optionally when two $R^x$ substituents are on adjacent atoms, they are combined to form a fused five, six or seven-membered carbocyclic or heterocyclic ring optionally substituted with from 1 to 3 substituents independently selected from halo, oxo, $C_{1-8}$ haloalkyl and $C_{1-8}$ alkyl;

each $R^{2a}$, $R^{2b}$ and $R^{2c}$ is independently selected from the group consisting of H, halogen, —CN, —$R^d$, —$CO_2R^e$, —$CONR^eR^f$, —C(O)$R^e$, —OC(O)$NR^eR^f$, —$NR^fC(O)R^e$, —$NR^fC(O)_2R^d$, —$NR^e$—C(O)$NR^eR^f$, —$NR^eR^f$, —$OR^e$, —O—$X^2$—$OR^e$, —O—$X^2$—$NR^eR^f$, —O—$X^2$—$CO_2R^e$, —O—$X^2$—$CONR^eR^f$, —$X^2$—$OR^e$, —$X^2$—$NR^eR^f$, —$X^2$—$CO_2R^e$, —$X^2$—$CONR^eR^f$, —$SF_5$, —$S(O)_2NR^eR^f$, $C_{6-10}$ aryl and $C_{5-10}$ heteroaryl, wherein each $X^2$ is a $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O and S, and optionally substituted with oxo; each $R^d$ is independently selected from the group consisting of $C_{1-8}$ alkyl, $C_{2-8}$ alkenyl, and $C_{1-8}$ haloalkyl;

$R^3$ is selected from the group consisting of —$NR^gR^h$ and $C_{4-12}$ heterocyclyl, wherein the $C_{4-12}$ heterocyclyl is optionally substituted with 1 to 6 $R^y$;

each $R^y$ is independently selected from the group consisting of
halogen, —CN, —$R^i$, —$CO_2R^j$, —$CONR^jR^k$, —CONH$C_{1-6}$ alkyl-OH, —C(O)$R^j$, —OC(O)$NR^jR^k$, —$NR^jC(O)R^k$, —$NR^jC(O)_2R^k$, CONOH, $PO_3H_2$, —$NR^j$—$C_{1-6}$ alkyl-C(O)$_2R^k$, —$NR^jC(O)NR^jR^k$, —$NR^jR^k$, —$OR^j$, —$S(O)_2NR^jR^k$, —O—$C_{1-6}$alkyl-$OR^j$, —O—$C_{1-6}$ alkyl-$NR^jR^k$, —O—$C_{1-6}$ alkyl-$CO_2R^j$, —O—$C_{1-6}$ alkyl-$CONR^jR^k$, —$C_{1-6}$ alkyl-$OR^j$, —$C_{1-6}$ alkyl-$NR^jR^k$, —$C_{1-6}$ alkyl-$CO_2R^j$, —$C_{1-6}$ alkyl-$CONR^jR^k$, and $SF_5$, wherein the $C_{1-6}$ alkyl portion of $R^y$ is optionally further substituted with OH, $SO_2NH_2$, $CONH_2$, CONOH, $PO_3H_2$, COO—$C_{1-8}$alkyl or $CO_2H$, wherein each $R^j$ and $R^k$ is independently selected from hydrogen, $C_{1-8}$ alkyl optionally substituted with 1 to 2 substituents selected from OH, $SO_2NH_2$, $CONH_2$, CONOH, $PO_3H_2$, COO—$C_{1-8}$alkyl or $CO_2H$, and $C_{1-8}$ haloalkyl optionally substituted with 1 to 2 substituents selected from OH, $SO_2NH_2$, $CONH_2$, CONOH, $PO_3H_2$, COO—$C_{1-8}$alkyl or $CO_2H$, or when attached to the same nitrogen atom $R^j$ and $R^k$ can be combined with the nitrogen atom to form a five or six-membered ring having from 0 to 2 additional heteroatoms as ring members selected from N, O or S, and optionally substituted with oxo; each $R^i$ is independently selected from the group consisting of —OH, $C_{1-8}$ alkyl, $C_{2-8}$ alkenyl, and $C_{1-8}$ haloalkyl each of which may be optionally substituted with OH, $SO_2NH_2$, $CONH_2$, CONOH, $PO_3H_2$, COO—$C_{1-8}$alkyl or $CO_2H$;

$R^g$ is selected from the group consisting of H, $C_{1-8}$ haloalkyl and $C_{1-8}$ alkyl;

$R^h$ is selected from —$C_{1-8}$ alkyl, $C_{1-8}$ haloalkyl, $C_{1-8}$ alkyl-COOH, $C_{1-8}$ alkyl-OH, $C_{1-8}$ alkyl-$CONH_2$, $C_{1-8}$ alkyl-$SO_2NH_2$, $C_{1-8}$ alkyl-$PO_3H_2$, $C_{1-8}$ alkyl-CONOH, $C_{1-8}$ alkyl-$NR^{h1}R^{h2}$, —C(O)—$C_{1-8}$alkyl, —C(O)—$C_{1-8}$alkyl-OH, —C(O)—$C_{1-8}$alkyl-COOH, $C_{3-10}$ cycloalkyl, —$C_{3-10}$ cycloalkyl-COOH, —$C_{3-10}$ cycloalkyl-OH, $C_{4-8}$ heterocyclyl, —$C_{4-8}$ heterocyclyl-COOH, —$C_{4-8}$ heterocyclyl-OH, —$C_{1-8}$ alkyl-$C_{4-8}$ heterocyclyl, —$C_{1-8}$ alkyl-$C_{3-10}$ cycloalkyl, $C_{5-10}$ heteroaryl, —$C_{1-8}$alkyl-$C_{5-10}$ heteroaryl, $C_{10}$ carbocyclyl, —$C_{1-8}$ alkyl-$C_{6-10}$ aryl, —$C_{1-8}$ alkyl-(C=O)—$C_{6-10}$ aryl, —$C_{1-8}$ alkyl-NH(C=O)—$C_{1-8}$ alkenyl, —$C_{1-8}$ alkyl-NH(C=O)—$C_{1-8}$ alkyl, —$C_{1-8}$ alkyl-NH(C=O)—$C_{1-8}$ alkynyl, —$C_{1-8}$ alkyl-(C=O)—NH—$C_{1-8}$ alkyl-COOH, and —$C_{1-8}$ alkyl-(C=O)—NH—$C_{1-8}$ alkyl-OH optionally substituted with $CO_2H$; or $R^h$ combined with the N to which it is attached is a mono-, di- or tri-peptide comprising 1-3 natural amino acids and 0-2 non-natural amino acids, wherein the non-natural aminoacids have an alpha carbon substituent selected from the group consisting of $C_{2-4}$ hydroxyalkyl, $C_{1-3}$ alkyl-guanidinyl, and $C_{1-4}$ alkyl-heteroaryl, the alpha carbon of each natural or non-natural amino acids are optionally further substituted with a methyl group, and the terminal moiety of the mono-, di-, or tri-peptide is selected from the group consisting of C(O)OH, C(O)O—$C_{1-6}$ alkyl, and $PO_3H_2$, wherein $R^{h1}$ and $R^{h2}$ are each independently selected from the group consisting of H, $C_{1-6}$ alkyl, and $C_{1-4}$ hydroxyalkyl;

the $C_{1-8}$ alkyl portions of $R^h$ are optionally further substituted with from 1 to 3 substituents independently selected from OH, COOH, $SO_2NH_2$, $CONH_2$, CONOH, COO—$C_{1-8}$ alkyl, $PO_3H_2$ and $C_{5-6}$ heteroaryl optionally substituted with 1 to 2 $C_{1-3}$ alkyl substituents, the $C_{10}$ carbocyclyl, $C_{5-10}$ heteroaryl and the $C_{6-10}$ aryl portions of $R^h$ are optionally substituted with 1 to 3 substituents independently selected from OH, $B(OH)_2$, COOH, $SO_2NH_2$, $CONH_2$, CONOH, $PO_3H_2$, COO—$C_{1-8}$alkyl, $C_{1-4}$alkyl, $C_{1-4}$alkyl-OH, $C_{1-4}$alkyl-$SO_2NH_2$, $C_{1-4}$alkyl $CONH_2$, $C_{1-4}$alkyl-CONOH, $C_{1-4}$alkyl-$PO_3H_2$, $C_{1-4}$alkyl-COOH, and phenyl and the $C_{4-8}$ heterocyclyl and $C_{3-10}$ cycloalkyl portions of $R^h$ are optionally substituted with 1 to 4 $R^w$ substituents;

each $R^w$ substituent is independently selected from $C_{1-4}$ alkyl, $C_{1-4}$ alkyl-OH, $C_{1-4}$ alkyl-COOH, $C_{1-4}$ alkyl-$SO_2NH_2$, $C_{1-4}$ alkyl $CONH_2$, $C_{1-4}$ alkyl-CONOH, $C_{1-4}$ alkyl-$PO_3H$, OH, COO—$C_{1-8}$ alkyl, COOH, $SO_2NH_2$, $CONH_2$, CONOH, $PO_3H_2$ and oxo;

$R^4$ is selected from the group consisting of O—$C_{1-8}$ alkyl, O—$C_{1-8}$ haloalkyl, O—$C_{1-8}$ alkyl-$R^z$, $C_{6-10}$ aryl, $C_{5-10}$ heteroaryl, —O—$C_{1-4}$ alkyl-$C_{6-10}$aryl and —O—$C_{1-4}$ alkyl-$C_{5-10}$ heteroaryl, wherein the $C_{6-10}$ aryl and the $C_{5-10}$ heteroaryl are optionally substituted with 1 to 5 $R^z$;

each $R^z$ is independently selected from the group consisting of halogen, —CN, —$R'''$, —$CO_2R''$, —$CONR''R^p$, —C(O)$R''$, —OC(O)NR''$R^p$, —NR''C(O)$R^p$, —NR''C(O)_2R'''$, —NR''—C(O)NR''$R^p$, —NR''$R^p$, —OR'', —O—$X^3$—OR'', —O—$X^3$—NR''$R^p$, —O—$X^3$—$CO_2R''$, —O—$X^3$—CONR''$R^p$, —$X^3$—OR'', —$X^3$—NR''$R^p$, —$X^3$—$CO_2R''$, —$X^3$—CONR''$R^p$, —$SF_5$, —S(O)$_2R''R^p$, —S(O)$_2NR''R^p$, and three to seven-membered carbocyclic or four to seven-membered heterocyclic ring wherein the three to seven-membered carbocyclic or four to seven-membered heterocyclic ring is optionally substituted with 1 to 5 $R^t$, wherein each $R^t$ is independently selected from the group consisting of $C_{1-8}$ alkyl, $C_{1-8}$haloalkyl, —$CO_2R''$, —CONR''$R^p$, —C(O)$R''$, —OC(O)NR''$R^p$, —NR''C(O)$R^p$, —NR''C(O)$_2R'''$, —NR''—C(O)NR''$R^p$, —NR''$R^p$, —OR'', —O—$X^3$—OR'', —O—$X^3$—NR''$R^p$, —O—$X^3$—$CO_2R''$, —O—$X^3$—CONR''$R^p$, —$X^3$—OR'', —$X^3$—NR''$R^p$, —$X^3$—$CO_2R''$, —$X^3$—CONR''$R^p$, —$SF_5$, and —S(O)$_2NR''R^p$;

wherein each $X^3$ is a $C_{1-4}$ alkylene; each $R''$ and $R^p$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R'''$ is independently selected from the group consisting of $C_{1-8}$ alkyl, $C_{2-8}$ alkenyl, and $C_{1-8}$ haloalkyl; and optionally when two $R^z$ substituents are on adjacent atoms, they are combined to form a fused five or six-membered carbocyclic or heterocyclic ring optionally substituted with oxo;

n is 0, 1, 2 or 3;

each $R^5$ is independently selected from the group consisting of halogen, —CN, —$R^q$, —$CO_2R^r$, —CONR'$R^s$, —C(O)$R^r$, —OC(O)NR'$R^s$, —NR'C(O)$R^s$, —NR'C(O)$_2R^q$, —NR'—C(O)NR'$R^s$, —NR'$R^s$, —OR', —O—$X^4$—OR', —O—$X^4$—NR'$R^s$, —O—$X^4$—$CO_2R^r$, —O—$X^4$—CONR'$R^s$, —$X^4$—OR', —$X^4$—NR'$R^s$, —$X^4$—$CO_2R^r$, —$X^4$—CONR'$R^s$, —$SF_5$, —S(O)$_2NR'R^s$, wherein each $X^4$ is a $C_{1-4}$ alkylene; each $R^r$ and $R^s$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^q$ is independently selected from the group consisting of $C_{1-8}$ alkyl, and $C_{1-8}$ haloalkyl;

$R^{6a}$ is selected from the group consisting of H, $C_{1-4}$ alkyl and $C_{1-4}$ haloalkyl;

each $R^{6b}$ is independently selected from the group consisting of F, $C_{1-4}$ alkyl, O—$R^u$, $C_{1-4}$ haloalkyl, $NR^uR^v$, wherein each $R^u$ and $R^v$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; and m is 0, 1, 2, 3 or 4.

In some embodiments, the small molecule PD-1/PD-L1 inhibitor is selected from the compounds or pharmaceutical compositions disclosed in WO 2018/005374 filed by ChemoCentryx on Jun. 26, 2017. The contents of which is incorporated herein for all purposes.

The PD-1 and/or PD-L1 inhibitors of the present disclosure can be formulated to retard the degradation of the compound or antibody or to minimize the immunogenicity of the antibody. A variety of techniques are known in the art to achieve this purposes.

IV. Pharmaceutical Compositions

The pharmaceutical compositions provided herein, such as those including compounds for modulating CCR2 activity and agents for blocking the PD-1/PD-L1 pathway can contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

Biological products such as antibodies of the present invention may be constituted in a pharmaceutical composition containing one or antibodies or a fragment thereof and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

The pharmaceutical compositions for the administration of the compounds and agents of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example, PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds and agents of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

The compounds and agents of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique. For instance, the compound and agent can be delivers to the tumor or the microenvironment surrounding the tumor.

In some embodiments, the compounds and agents may be deposited within a medical device, such as a stent, and delivered to the treatment site for treatment of a portion of the body. Stents have been used as delivery vehicles for therapeutic agents. Intravascular stents are generally permanently implanted in coronary or peripheral vessels. Stent designs include those of U.S. Pat. Nos. 4,733,655; 4,800,882; and 4,886,062. Such designs include both metal and polymeric stents, as well as self-expanding and balloon-expandable stents. Stents may also used to deliver therapeutic agents at the site of contact with the vasculature, as disclosed in U.S. Pat. No. 5,102,417 and International Patent Application Nos. WO 91/12779 and WO 90/13332, U.S. Pat. Nos. 5,419,760 and 5,429,634, for example.

The term "deposited" means that the compound and agent are coated, adsorbed, placed, or otherwise incorporated into the device by methods known in the art. For example, the compound and agent may be embedded and released from within ("matrix type") or surrounded by and released through ("reservoir type") polymer materials that coat or span the medical device. In the later example, the compound and agent may be entrapped within the polymer materials or coupled to the polymer materials using one or more the techniques for generating such materials known in the art. In other formulations, the compound and agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the compound and agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable popolymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

In some embodiments, the compound and agent are formulated for release from the polymer coating into the environment in which the medical device is placed. Preferably, the compound and agent are released in a controlled manner over an extended time frame (e.g., weeks or months) using at least one of several well-known techniques involving polymer carriers or layers to control elution. Some of these techniques were previously described in U.S. Patent App. Publ. No. 20040243225.

V. Methods of Administration of Combination Therapy

In another aspect, the present disclosure provides a combination therapy for the treatment of cancer. The combination therapy includes a therapeutically effective amount of a CCR2 antagonist and a therapeutically effective amount of a PD-1 and/or PD-L1 inhibitor. The combination of therapeutic agents can act synergistically to effect the treatment or prevention of cancer.

Depending on the disease status and the subject's condition, the compounds, antibodies, and formulations of the present disclosure may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration. In addition, the compounds and antibodies may be formulated, alone or together, in suitable dosage unit formulations containing conventional nontoxic pharmaceutically acceptable carriers, adjuvants and vehicles appropriate for each rouse of administration. The present disclosure also contemplates administration of the compounds and antibodies of the present disclosure in a depot formulation.

It will be understood, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In the treatment of cancers, e.g., solid tumors which require chemokine receptor modulation, an appropriate dosage level of a CCR2 antagonist will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

An appropriate dosage level of a PD-1 inhibitor and/or a PD-L1 inhibitor will generally be about 0.0001 to about 100 mg/kg, usually from about 0.001 to about 20 mg/kg, and more usually from about 0.01 to about 10 mg/kg, of the subject's body weight. Preferably, the dosage is within the range of 0.1-10 mg/kg body weight. For example, dosages can be 0.1, 0.3, 1, 3, 5 or 10 mg/kg body weight, and more preferably, 0.3, 1, 3, or 10 mg/kg body weight. The dosing schedule can typically be designed to achieve exposures that result in sustained receptor occupancy (RO) based on typical pharmacokinetic properties of an antibody. An exemplary treatment regime of antibodies entails administration once per week, once every two weeks, once every three weeks, once every four weeks, once a month, once every 3 months or once every three to 6 months. For example, a dosing schedule may comprise administering an antibody: (i) every two weeks in 6-week cycles; (ii) every four weeks for six dosages, then every three months; (iii) every three weeks; (iv) 3-10 mg/kg body weight once followed by 1 mg/kg body weight every 2-3 weeks. Considering that an IgG4 antibody typically has a half-life of 2-3 weeks, a preferred dosage regimen for an anti-PD-1 or anti-PD-L1 antibody comprises 0.3-10 mg/kg body weight, preferably 3-10 mg/kg body weight, more preferably 3 mg/kg body weight via intravenous administration, with the antibody being given every 14 days in up to 6-week or 12-week cycles until complete response or confirmed progressive disease. An exemplary treatment regime of small molecules entails administration daily, twice per week, three times per week, or once per week. The dosage and scheduling may change during a course of treatment.

In some embodiments, two or more antibodies with different binding specificities are administered simultaneously, in which case the dosage of each antibody administered falls within the ranges indicated. The antibody can be administered on multiple occasions. Intervals between single dosages can be, for example, weekly, every 2 weeks, every 3 weeks, monthly, every three months or yearly. Intervals can also be irregular as indicated by measuring blood levels of antibody to the target antigen in the patient. In some methods, dosage is adjusted to achieve a plasma antibody concentration of about 1-1000 mg/ml and in some methods about 25-300 mg/ml.

The therapeutic compound and agent in the combination therapy disclosed herein may be administered either alone or in a pharmaceutical composition which comprises the therapeutic compound and agent and one or more pharmaceutically acceptable carriers, excipients and diluents.

In some embodiments, the therapeutic compound and agent are each provided in an amount that would be sub-therapeutic if provided alone or without the other. Those of skill in the art will appreciate that "combinations" can involve combinations in treatments (i.e., two or more drugs can be administered as a mixture, or at least concurrently or at least introduced into a subject at different times but such that both are in a subject at the same time).

Likewise, compounds, agents and compositions of the present invention may be used in combination with other drugs that are used in the treatment, prevention, suppression or amelioration of cancer. Such other drugs may be administered, by a route and in an amount commonly used therefor, contemporaneously or sequentially with a compound, agent or composition of the present invention. When a compound, agent or composition of the present invention is used contemporaneously with one or more other drugs, a pharmaceutical composition containing such other drugs in addition to the compound, agent or composition of the present invention is preferred. Accordingly, pharmaceutical compositions can include those that also contain one or more other active ingredients or therapeutic agents, in addition to a compound, agent or composition of the present invention.

Combination therapy includes co-administration of the CCR2 antagonist and the PD-1 and/or PD-L1 inhibitor, sequential administration of the CCR2 antagonist and the PD-1 and/or PD-L1 inhibitor, administration of a composition containing the CCR2 antagonist and the PD-1 and/or PD-L1 inhibitor, or simultaneous administration of separate compositions such that one composition contains the CCR2 antagonist and another composition contains the PD-1 and/or PD-L1 inhibitor.

Co-administration includes administering the CCR2 antagonist of the present invention within 0.5, 1, 2, 4, 6, 8, 10, 12, 16, 20, or 24 hours of the PD-1 and/or PD-L1 inhibitor of the present invention. Co-administration also includes administering simultaneously, approximately simultaneously (e.g., within about 1, 5, 10, 15, 20, or 30 minutes of each other), or sequentially in any order. Moreover, the CCR2 antagonist and PD-1 and/or PD-L1inhibitor can each be administered once a day, or two, three, or more times per day so as to provide the preferred dosage level per day.

VI. Kits

In some aspects, provided herein are kits containing a CCR2 chemokine receptor antagonist and a PD-1 and/or PD-L1 inhibitor disclosed herein that are useful for treating a cancer. A kit can contain a pharmaceutical composition containing a CCR2 chemokine receptor antagonist compound, e.g., a small molecule inhibitor of CCR2 and a pharmaceutical composition containing an PD-1 and/or PD-L1, e.g., an antibody inhibitor. In some instances, the kit includes written materials e.g., instructions for use of the compound, antibody or pharmaceutical compositions thereof. Without limitation, the kit may include buffers, diluents, filters, needles, syringes, and package inserts with instructions for performing any methods disclosed herein.

Suitable CCR2 chemokine receptor antagonist and PD-1 and/or PD-L1 inhibitors include the compounds described herein.

VII. Examples

Example 1: Administration of a CCR2 Inhibitor Enhances Anti-PD-1 Therapy

CT26 tumors are heavily infiltrated by cytotoxic T cells and other leukocytes, but nevertheless grow rapidly in Balb/c mice after subcutaneous implantation. These tumors are partially responsive to treatment with anti-PD-1 and anti-CTLA monoclonal antibody therapies.

Six days after subcutaneous CT26 implantation into the flanks of 9 wk female Balb/c mice ($2.5 \times 10^5$/mouse), the recipients were randomized based on tumor size and treatment was begun. Mice received anti-PD-1 (RPM1-14 from BioXcell, Inc., catalog number BE0146) by IP injection on days 7, 10, 17 and 21 (200 μg/mouse), and received CCR2 antagonist Compound 1 (30 or 60 mg/kg) or vehicle by oral gavage every 24 hours starting day 7.

We have found that the therapeutic effects of anti-PD-1 therapy are appreciably enhanced by specific blockade of chemokine receptor 2 (CCR2) via a small molecule antagonist. This combined anti-PD-1/CCR2i approach significantly decreases tumor size and increases the proportion of long-term survivors, with more than 50% of the mice (up to 73%) showing complete regression of a previously established tumor. The effects of this combined therapy are dependent on the presence of CD8$^+$ T cells, as tumors do not respond to the therapy in CD8-depleted mice. The anti-CT26 tumor response is specific: long term survivors are resistant to re-inoculation with the CT26 tumor (even without further dosing of either drug) but are not resistant to the 4T1 breast tumor. CCR2 antagonism alters the tumor microenvironment by reducing the number of mMDSC per gram of tumor (a CCR2$^{hi}$ population phenotypically defined as CD11b$^+$/Ly6G$^-$/Ly6C$^{hi}$). Reduction in tumor size is inversely proportional to the ratio of CD8 T cells to mMDSC. The data from the CT26 model are provided in the following paragraphs.

FIG. 1 shows immunohistochemistry analysis of normal and human tumor tissue using anti-hCCR2 Mab. Panels A and B show normal colon tissue at 40× and 200×, respectively. Panels C, D, E, and F, show human representative colon cancer tissue at the magnifications indicated. Specific CCR2 staining was observed on 78 malignant tumors (diagnosed Grade I-III) from colon carcinoma patients but not on normal control colon tissues.

CT26 is a Balb/c-derived colon adenocarcinoma that generates tumors when injected subcutaneously into Balb/c mice. Single cells were isolated from established subcutaneous CT26 tumors (28 days after injection) by mincing, digesting the tissue briefly with collagenase-D, and passing the slurry through 100 μm sieves. Cells were stained for flow cytometry and gated on live CD45$^+$ tumor-infiltrating leukocytes (FIG. 2). Comparison between staining with α-mouse CCR2 Mab (FIG. 2A) and its isotype-matched control (FIG. 2B) revealed CCR2-specific staining on a subset of CD11b$^+$ leukocytes.

Figures 3A, 3B:
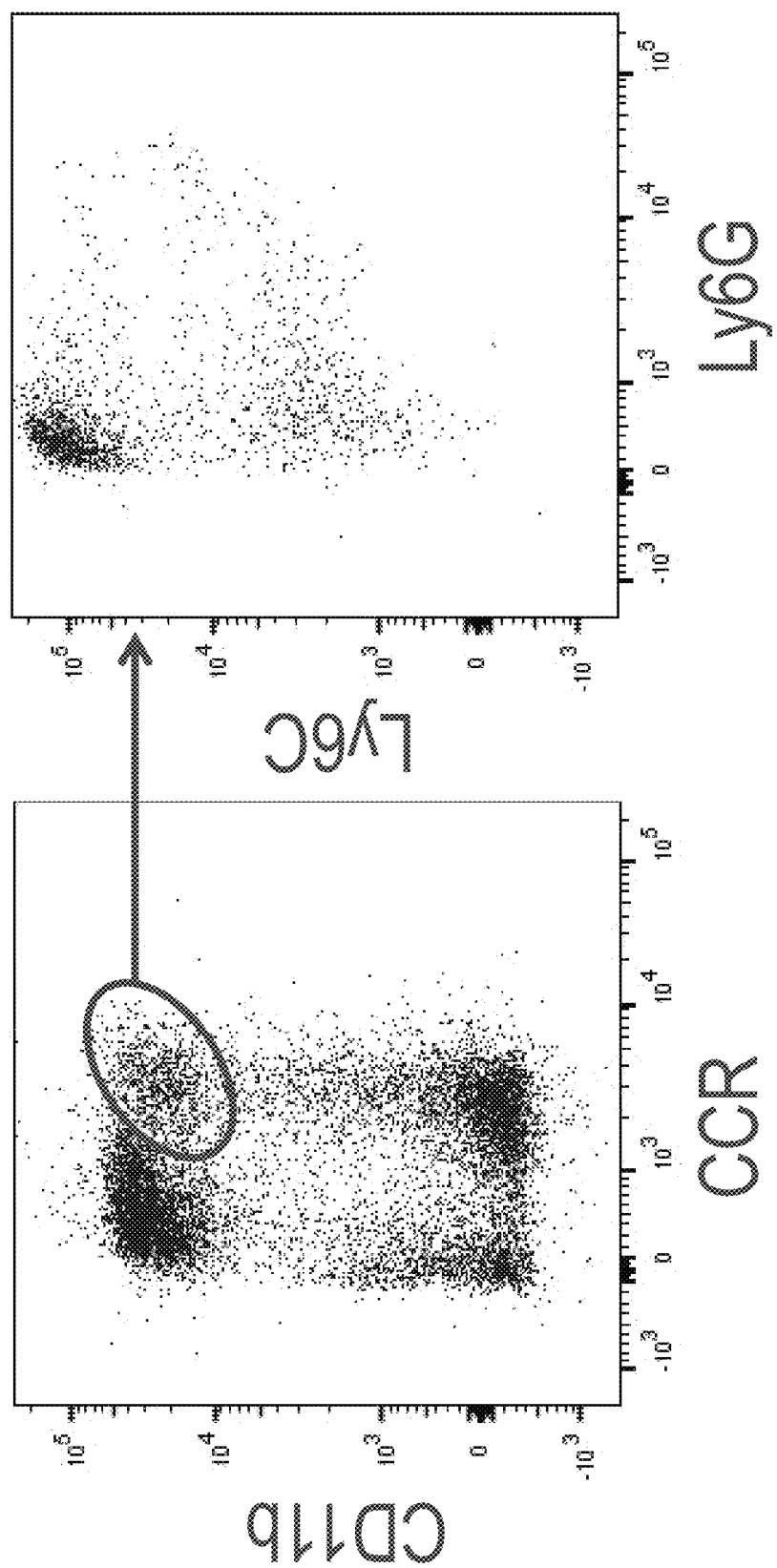
FIGS. 3A and 3B illustrate that the CD11b$^+$/CCR2$^+$ population within CT26 tumors comprises predominantly the Ly6C$^{hi}$/Ly6G$^{neg}$ Monocytic Myeloid-Derived Suppressor Cell (M-MDSC) Immunophenotype. Panel A plots the data obtained using a CD11b$^+$/CCR2$^+$ markers and CD45$^+$ gating. Panel B plots the data obtain looking at the CD11b$^+$/CCR2$^+$ subset using Ly6C/Ly6G markers.

Gating on the CCR2$^+$ population FIG. 3B shows these cells express high levels of Ly6C and to lack Ly6G; hallmarks of M-MDSCs. Such cells are implicated in anergy-induction of tumor-specific cytotoxic T cell populations.

Figures 4A, 4B, 4C:
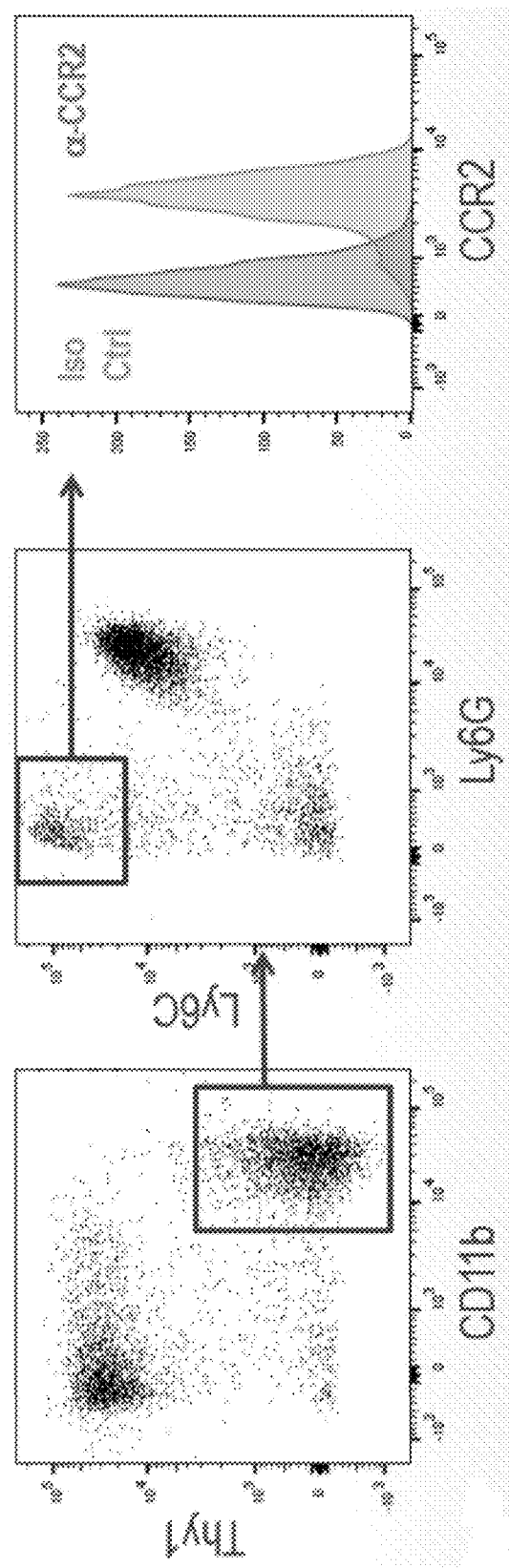
FIGS. 4A-4C show direct gating on M-MDSC cells isolated from CT26 tumors, demonstrating robust CCR2 expression. Panel A: gating live CD45$^+$ CT26-Infiltrating cells on CD11b$^+$ population. Panel B: gating LyC$^{hi}$/Ly6G$^-$ population. Panel C: histogram overlay of CCR2 staining (right) on isotype-matched control Mab staining (left) of the Ly6C$^{hi}$/Ly6G$^-$ population.

FIG. 4 shows direct gating on M-MDSC cells isolated from CT26 tumors demonstrates robust CCR2 expression. Panel A: gating live CD45$^+$ CT26-Infiltrating cells on CD11b$^+$ population. Panel B: gating LyC$^{hi}$/Ly6G$^-$ population. Panel C: histogram overlay of CCR2 staining (right) on isotype-matched control Mab staining (left) of the Ly6C$^{hi}$/Ly6G$^-$ population.

Figure 5:
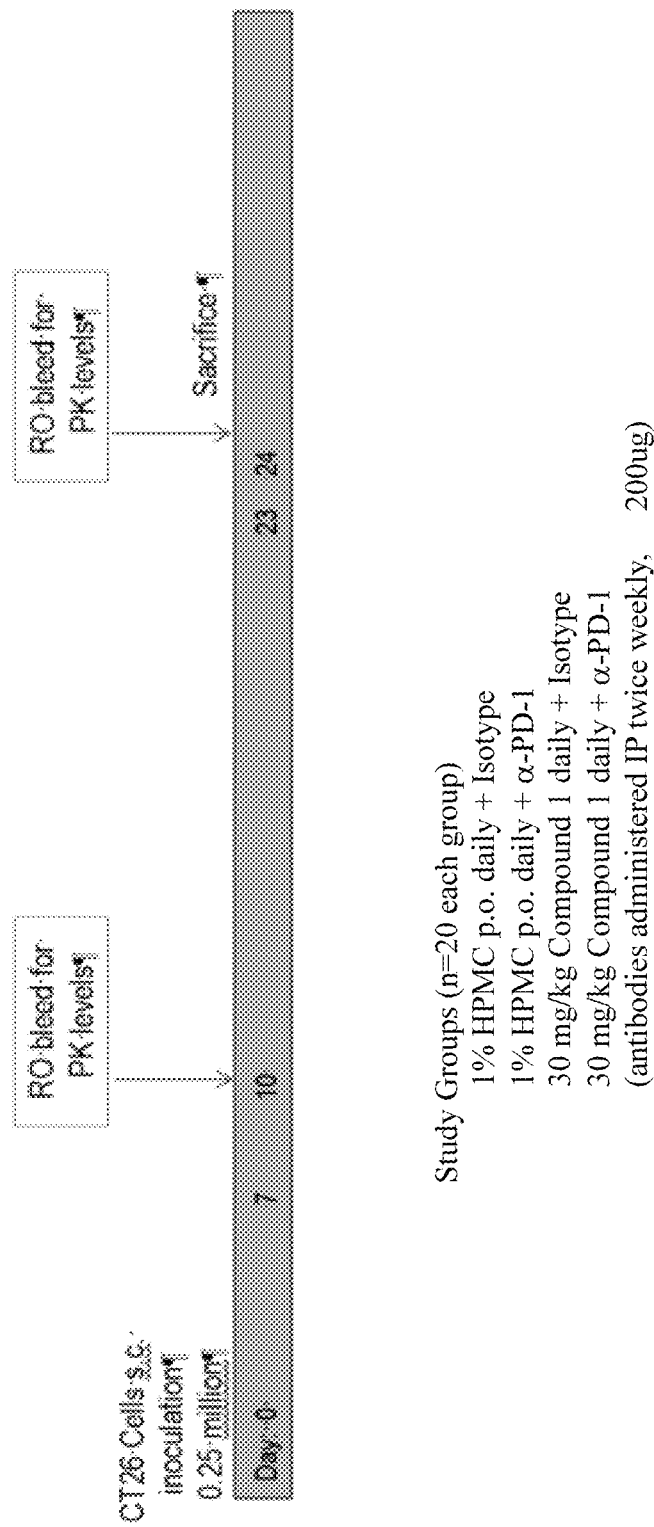
FIG. 5 illustrates the general study design for anti-PD-1+ Compound 1 in CT26 model.

FIG. 5 illustrates the general study design for anti-PD-1+ Compound 1 in CT26 model.

Figure 6A:
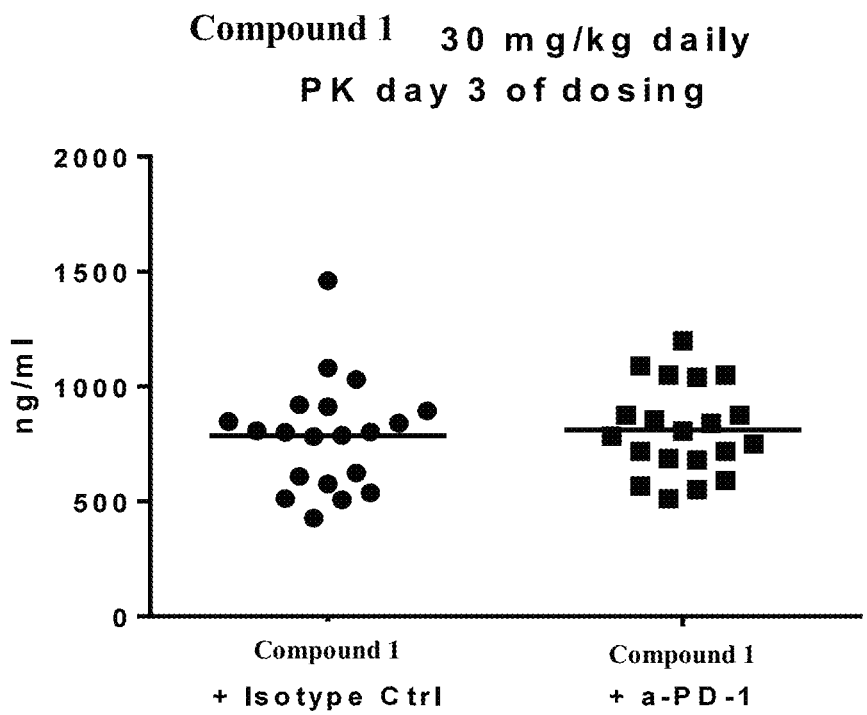
FIGS. 6A-6B show that Compound 1 dosed via oral gavage at 30 mg/kg daily provides trough plasma levels at or above those required for full receptor coverage. Panel A shows Compound 1 plasma levels at day 3 of dosing. Panel B shows Compound 1 at 23 days of dosing.
Figure 6B:
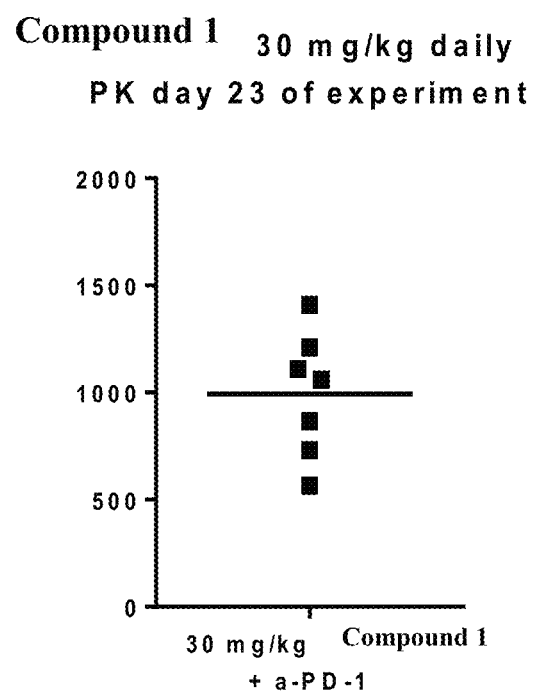

FIG. 6 shows that Compound 1 dosed via oral gavage at 30 mg/kg daily provides trough plasma levels at or above those required for full receptor coverage. Panel A shows Compound 1 plasma levels at day 3 of dosing. Panel B shows Compound 1 at 23 days of dosing.

Figure 7A:
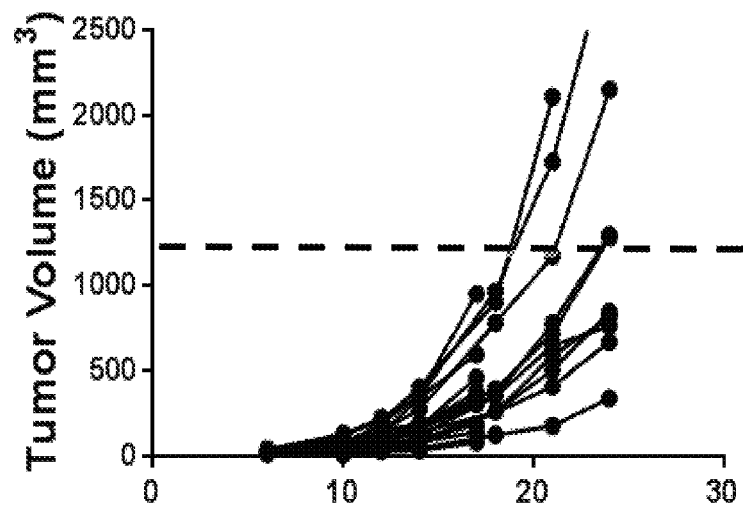
FIGS. 7A-7B show that the combination of Compound 1 and α-PD-1 results in smaller tumor volumes. Panel A shows mice dosed with 1% HPMC+Isotype. Panel B shows mice dosed with 1% HPMC+α-PD-1. Panel C shows mice dosed with 30 mg/kg Compound 1+Isotype. Panel D shows mice dosed with 30 mg/kg Compound 1+α-PD-1. The dotted line indicates the largest tumor volume observed in the Compound 1+α-PD-1 group. "1% HPMC" is the vehicle control for Compound 1, "isotype" is the identically-dosed isotype-matched control for α-PD-1.
Figure 7B:
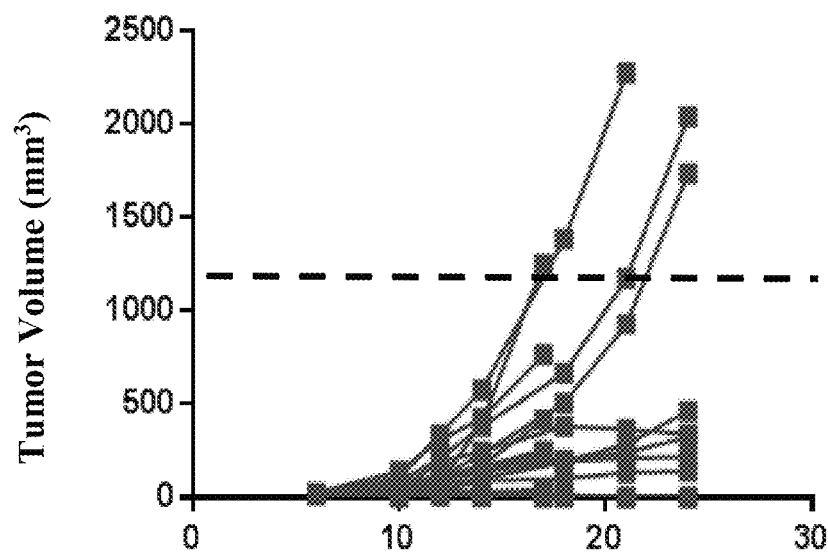

FIG. 7 shows that the combination of Compound 1 and α-PD-1 results in smaller tumor volumes. Panel A shows mice dose with 1% HPMC+Isotype. Panel B shows mice dosed with 1% HPMC+α-PD-1. Panel C shows mice dosed with 30 mg/kg Compound 1+Isotype. Panel D shows mice dose with 30 mg/kg Compound 1+α-PD-1. The dotted line indicates the largest tumor volume observed in the Compound 1+α-PD-1 group. "1% HPMC" is the vehicle control for Compound 1, "isotype" is the identically-dosed isotype-matched control for α-PD-1. As seen in FIG. 7 α-PD-1 alone reduces CT26 tumor volume, but combination with Compound 1 enhances this effect.

Figure 8:
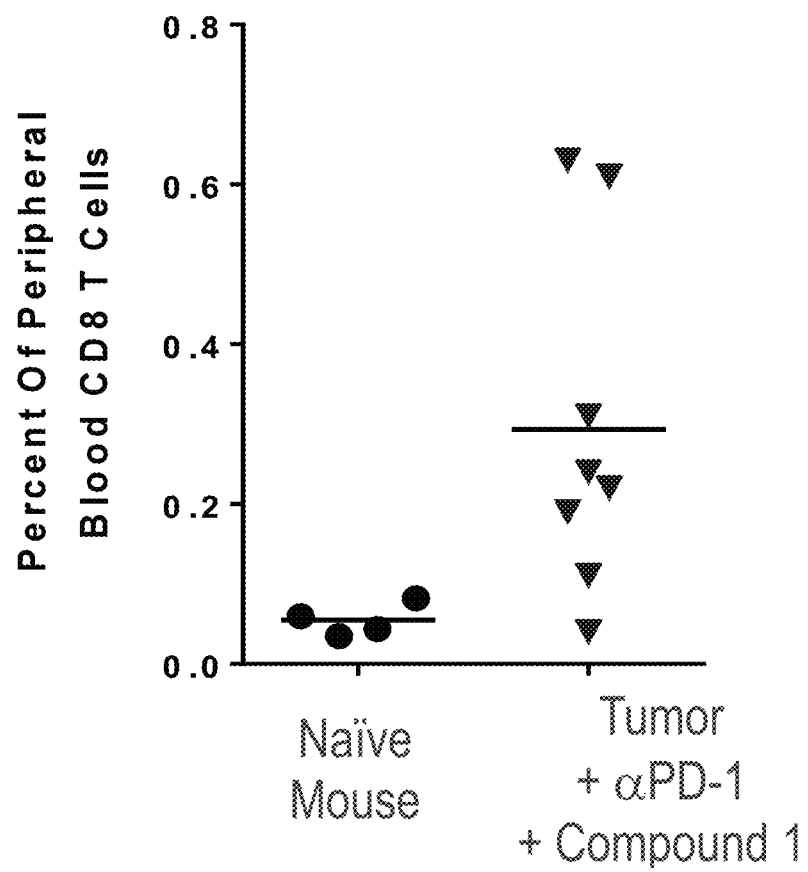
FIG. 8 shows staining peripheral blood lymphocytes with peptide/Class I tetramer for the immunodominant CT26 antigen demonstrates a CT26-specific CD8 T cells response in Tumor-Bearing Mice.

Staining peripheral blood lymphocytes with peptide/Class I tetramer for the immunodominant CT26 antigen demonstrates a CT26-specific CD8 T cells response in Tumor-Bearing Mice FIG. 8. AH1, the immunodominant peptide for cytotoxic T cell response against CT26, is derived from the gp70 protein of a MuLV retrovirus endogenous to CT26. AH1 specific T cell receptors are largely absent from the peripheral blood CD8 T cells of naive mice, but abundant on the same population of CT26 tumor-bearing mice.

Figures 9A, 9B, 9C:
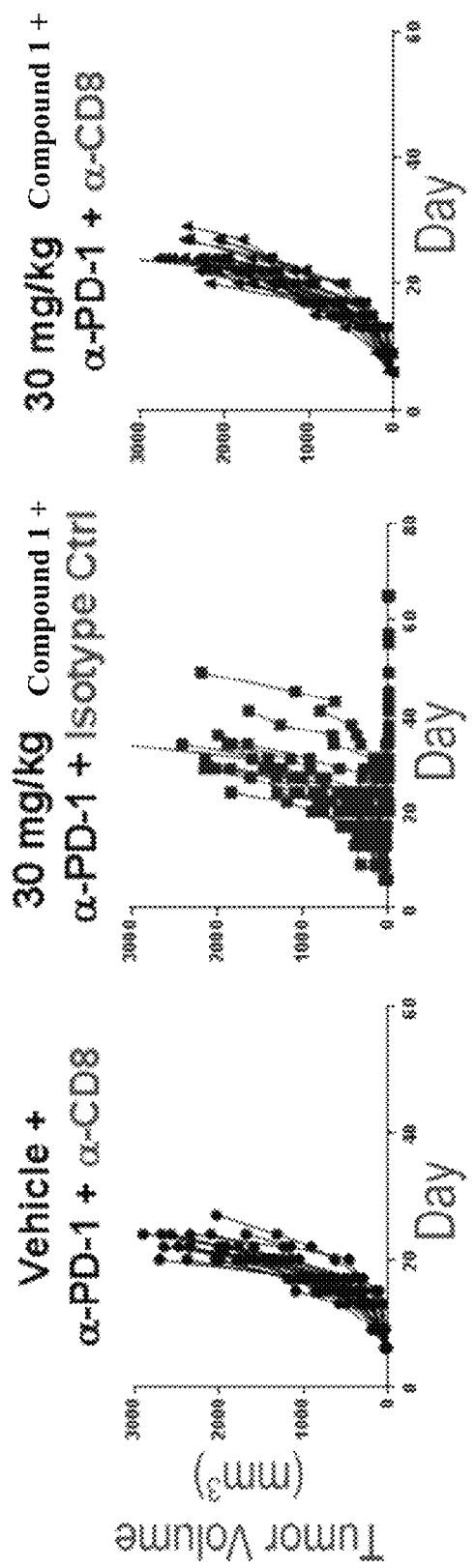
FIGS. 9A-9C demonstrate that the reduction in tumor size induced by Compound 1+α-PD-1 therapy requires CD8 T Cells. Panel A: shows tumor volume in mice treated with Vehicle+α-PD-1+α-CD8. Panel B: shows tumor volume in mice treated with 30 mg/kg Compound 1+α-PD-1+isotype control. Panel C: shows tumor volume in mice treated with 30 mg/kg Compound 1+α-PD-1+α-CD8.

FIG. 9 demonstrates that the reduction in tumor size induced by Compound 1+α-PD-1 therapy requires CD8 T Cells. Panel A: shows tumor volume in mice treated with Vehicle+α-PD-1+α-CD8. Panel B: shows tumor volume in mice treated with 30 mg/kg Compound 1+α-PD-1+isotype control. Panel C: shows tumor volume in mice treated with 30 mg/kg Compound 1+α-PD-1+α-CD8.

Figure 10:
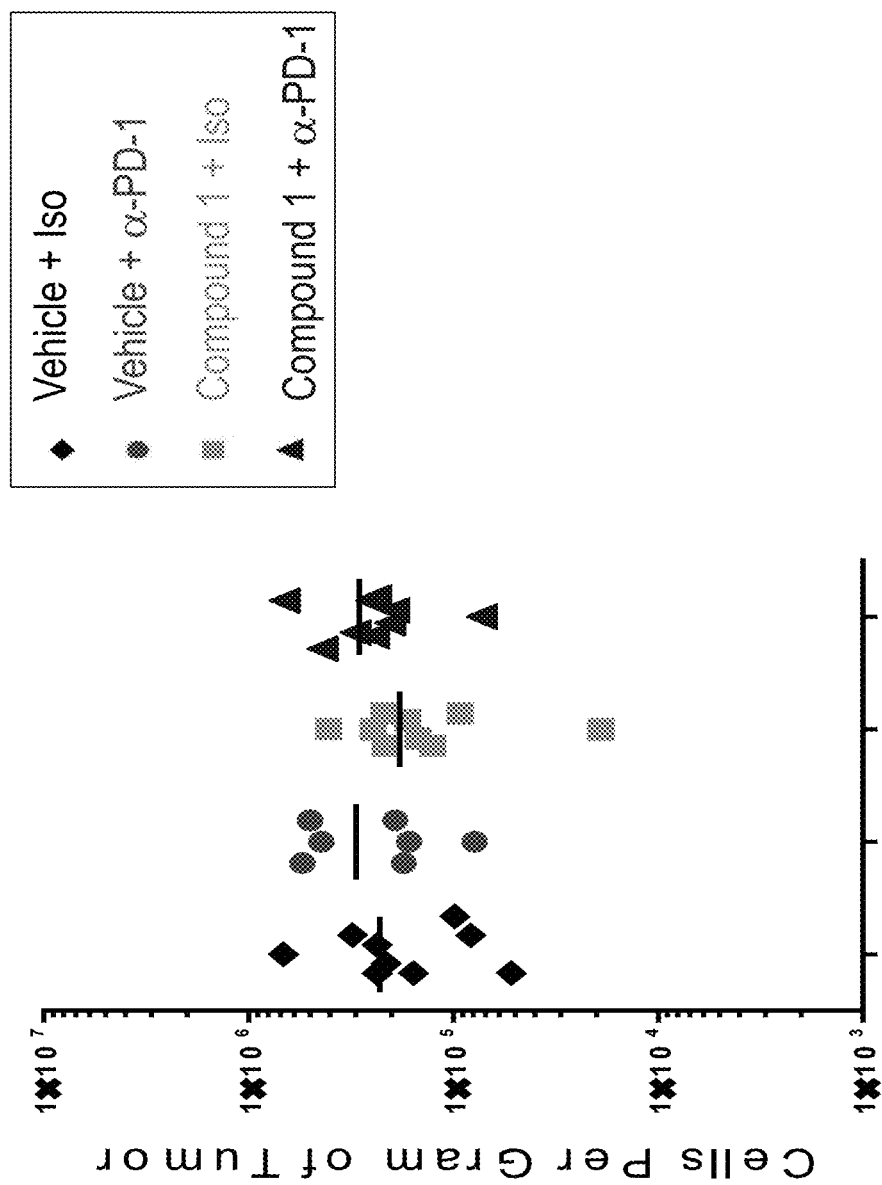
FIG. 10 demonstrates that despite the involvement of cytotoxic T cells in tumor size reduction, tumor CD8 T cell counts are not significantly changed by treatment. Tumor-infiltrating cytotoxic T cells (Thy1$^+$/CD8$^+$) were quantitated by weighing the tumors before dissociation, allowing cells-per-gram of tumor to be calculated.

FIG. 10 demonstrates that despite the involvement of cytotoxic T cells in tumor size reduction, tumor CD8 T cell counts are not significantly changed by treatment. Tumor-infiltrating cytotoxic T cells (Thy1$^+$/CD8$^+$) were quantitated by weighing the tumors before dissociation, allowing cells-per-gram of tumor to be calculated.

Figure 11:
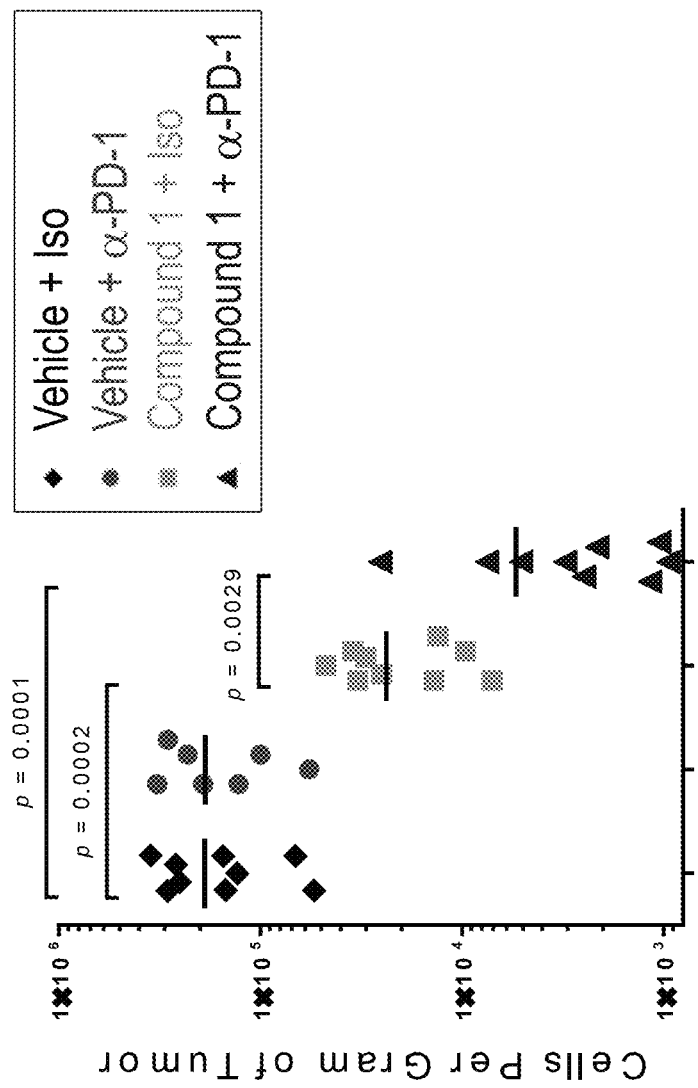
FIG. 11 shows that Compound 1 reduces M-MDSCs in the CT26 Tumor Micro environment by day 24. M-MDSCs were quantitated by weighing the tumors before dissociation, allowing cells-per-gram of tumor to be calculated.

FIG. 11 shows that Compound 1 reduces M-MDSCs in the CT26 Tumor Micro environment by day 24. M-MDSCs were quantitated by weighing the tumors before dissociation, allowing cells-per-gram of tumor to be calculated. As seen in the figure, Compound 1 alone reduces the population of M-MDSCs, but the combination with α-PD-1 enhances the effect.

Figure 12:
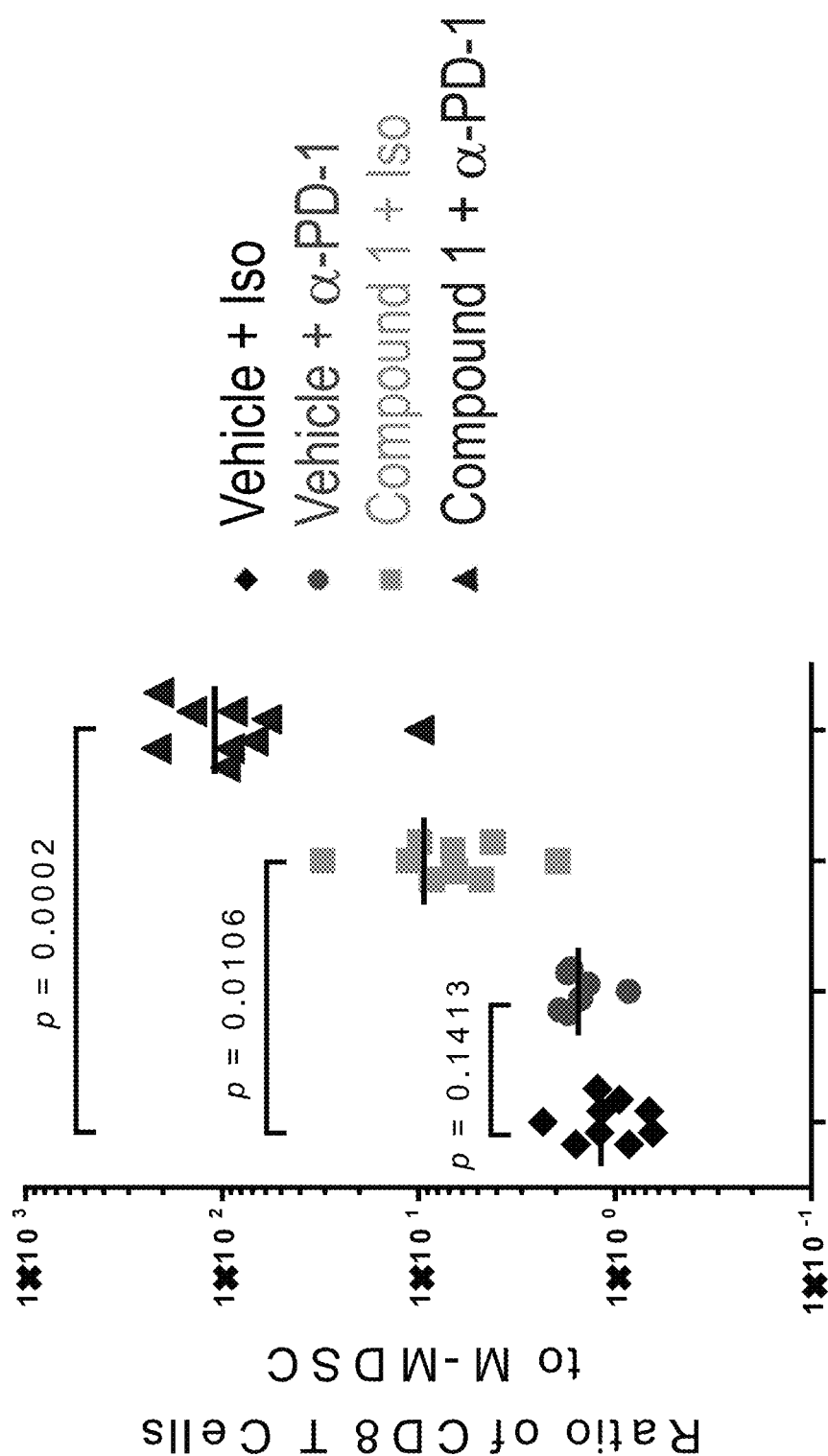
FIG. 12 shows that the ratio of CD8 T cells to M-MDSCs is significantly increased by combination treatment. The ratio of CD8 T cells and M-MDSCs was calculated from the cell counts shown in FIG. 10 and FIG. 11. The ratio in control treated mice (veh+iso) was 1:1, meaning one M-MDSC for every CD8 T cell. Combined treatment reduced the M-MDSC to the advantage of CD8 T cells, yielding 100 CD8 T cells for every M-MDSC. Treatment of Compound 1 alone yielded 10 CD8 T cells for every M-MDSC cell. Treatment with α-PD-1 CD8 T cells for every M-MDSC cell.

FIG. 12 shows that the ratio of CD8 T cells to M-MDSCs is significantly increased by combination treatment. The ratio of CD8 T cells and M-MDSCs was calculated from the cell counts shown in FIG. 10 and FIG. 11. The ratio in control treated mice (veh+iso) was 1:1, meaning one M-MDSC for every CD8 T cell. Combined treatment reduced the M-MDSC to the advantage of CD8 T cells, yielding 100 CD8 T cells for every M-MDSC. Treatment of Compound 1 alone yielded 10 CD8 T cells for every M-MDSC cell. Treatment with α-PD-1 CD8 T cells for every M-MDSC cell.

Figure 13:
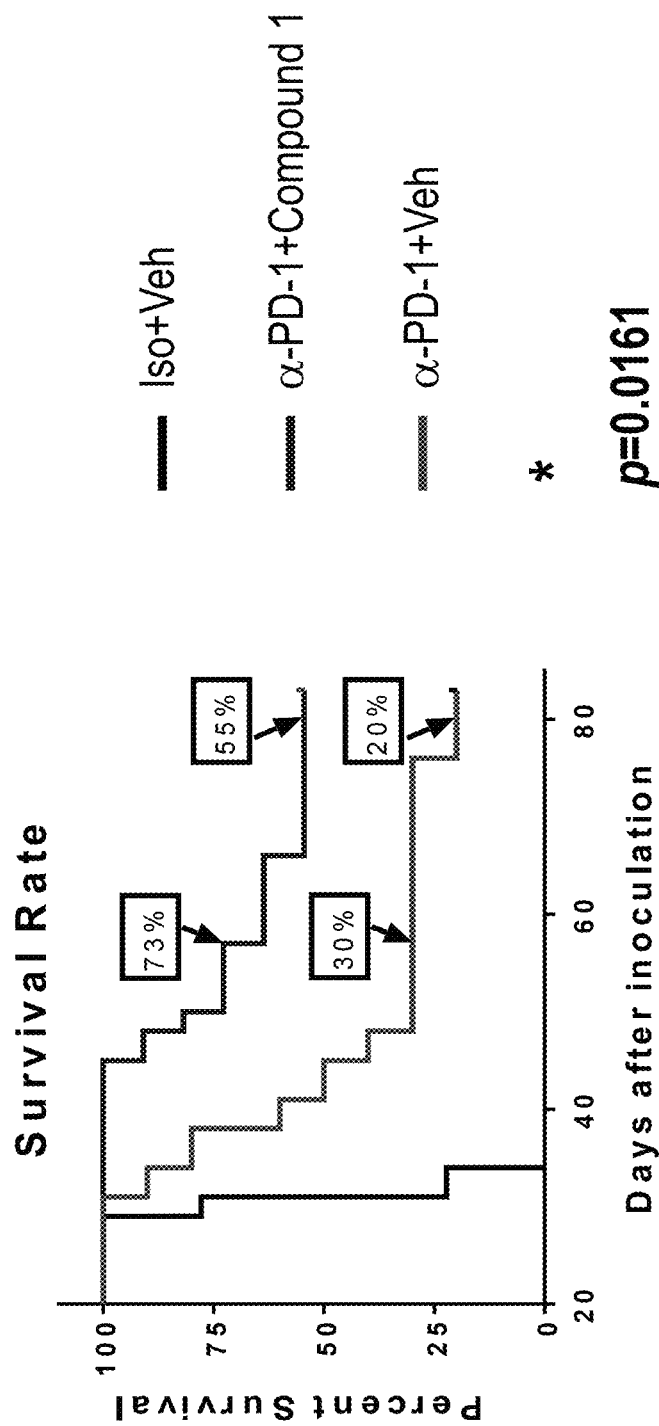
FIG. 13 shows that the number of CT26 Long-Term survivors in response to α-PD-1 are enhanced by CCR2 combination treatment. At day 83, 6 survivors remained in the α-PD-1+Compound 1 group while only 2 survivors remained in the α-PD-1+Veh group. Subgroups of mice taken out on day 27 for cell analysis were excluded from this survival rate analysis. One mouse in the Iso+Veh group and one in the α-PD-1+ 598 group never developed tumor, and these two mice were excluded from this analysis. Gehan-Breslow-Wilcoxan test used to determine p value between red (middle) and blue (upper) curves.

FIG. 13 shows that the number of CT26 Long-Term survivors in response to α-PD-1 are enhanced by CCR2 combination treatment. At day 83, 6 survivors remained in the α-PD-1+Compound 1 group while only 2 survivors remained in the α-PD-1+Veh group. Subgroups of mice taken out on day 27 for cell analysis were excluded from this survival rate analysis. One mouse in the Iso+Veh group and one in the α-PD-1+598 group never developed tumor, and these two mice were excluded from this analysis. Gehan-Breslow-Wilcoxan test used to determine p value between red (middle) and blue (upper) curves.

Figures 14A, 14B:
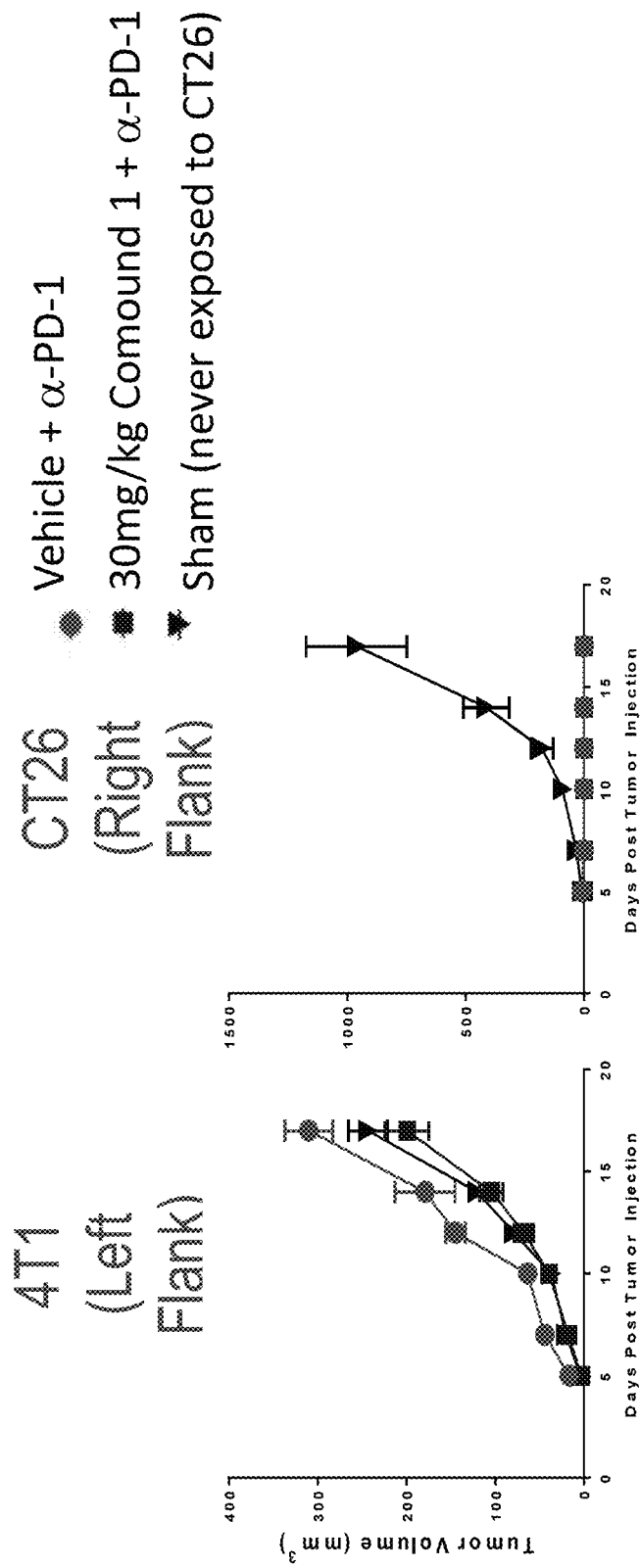
FIGS. 14A and 14B show long-term survivors possess specific immunity to re-inoculation with CT26 (Panel B), but not to the 4T1 breast tumor (Panel A).

CT26 survivor mice previously treated with α-PD-1 with or without Compound 1, tumor free for 2-4 weeks, were re-inoculated with CT26 on the right flank, and inoculated with 4T1 (for the first time) on the left flank. CT26 grew only on mice that were not previously exposed to CT26 FIG. 14B. 4T1 grew on all mice regardless of previous CT26 exposure FIG. 14A.

These data are consistent with a hypothesis that CCR2 antagonism enhances anti-PD-1 therapy by preventing mMDSC from accumulating within the tumor, thus reducing their suppressive effects on cytotoxic T cells.

In addition to colon cancer, CCR2 blockade has shown efficacy in mouse models of glioblastoma, and pancreatic cancer, as well as in human pancreatic cancer.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating colorectal cancer in a mammal, said method comprising administering a therapeutically effective amount of a CCR2 chemokine receptor antagonist and a therapeutically effective amount of a PD-1 and/or PD-L1 inhibitor, wherein said CCR2 chemokine receptor antagonist is a compound of Formula (Ia4)

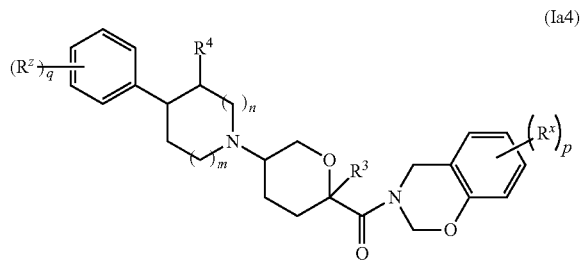

or a pharmaceutically acceptable salt thereof; wherein
the subscripts m and n are each independently 1;
$R^3$ is selected from the group consisting of $C_{1-8}$ alkyl and $C_{3-8}$ cycloalkyl;
$R^4$ is selected from the group consisting of H and $C_{1-8}$ alkyl;
the subscript p is 1 or 2;
each $R^x$ is independently selected from the group consisting of halogen, —$R^c$, —$OR^a$, —O—$X^1$—$OR^a$, and —$X^1$—$OR^a$, wherein each $X^1$ is a $C_{1-4}$ alkylene; each $R^a$ is selected from hydrogen, $C_{1-8}$ alkyl, and $C_{1-8}$ haloalkyl; each $R^c$ is independently selected from the group consisting of $C_{1-8}$ alkyl and $C_{1-8}$ haloalkyl;
the subscript q is 1 or 2;

each $R^z$ is independently selected from the group consisting of halogen, —$R^i$, —$CO_2R^g$, and tetrazole; wherein each $R^9$ is selected from hydrogen, $C_{1-8}$ alkyl, and $C_{1-8}$ haloalkyl; each $R^i$ is independently selected from the group consisting of $C_{1-8}$ alkyl, and $C_{1-8}$ haloalkyl.

2. The method of claim 1, wherein the said CCR2 inhibitor has the formula

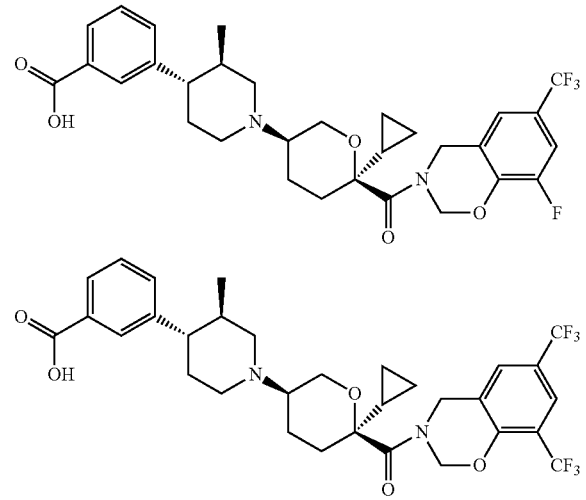

or a pharmaceutically acceptable salt thereof.

3. The method of claim 1, wherein said CCR2 inhibitor has the formula (Compound 1)

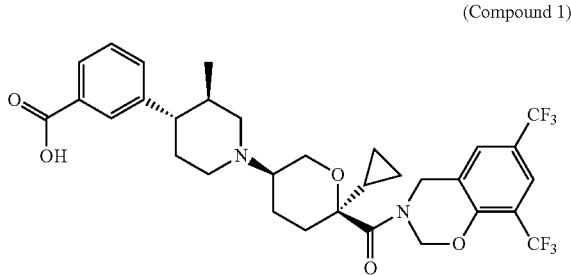 [SMILES: C[C@H]1CN([C@@H]2CC[C@@](C(=O)N3COc4c(F)cc(C(F)(F)F)cc4C3)(C3CC3)OC2)CC[C@@H]1c1cccc(C(=O)O)c1]

or a pharmaceutically acceptable salt thereof.

4. The method of claim 1, wherein said CCR2 inhibitor has the formula (Compound 2)

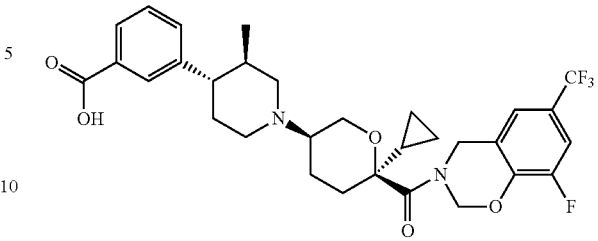

or a pharmaceutically acceptable salt thereof.

5. The method of claim 1, wherein said PD-1 and/or PD-L1 inhibitor is a PD-1 inhibitor.

6. The method of claim 5 wherein the PD-1 inhibitor is selected from the group consisting of pembrolizumab, nivolumab, IBI-308, mDX-400, BGB-108, MED-0680, SHR-1210, PF-06801591, PDR-001, GB-226, and STI-1110.

7. The method of claim 5, wherein the PD-1 inhibitor is selected from the group consisting of Nivolumab, Pembrolizumab, and Pidilizumab.

8. The method of claim 1, wherein said PD-1 and/or PD-L1 inhibitor is a PD-L1 inhibitor.

9. The method of claim 8, wherein the PD-L1 inhibitor is selected from the group consisting of durvalumab, atezolizumab, avelumab, BMS-936559, ALN-PDL, TSR-042, KD-033, CA-170, CA-327, STI-1014, and KY-1003.

10. The method of claim 1, wherein the CCR2 chemokine receptor antagonist and the PD-1 inhibitor and/or the PD-L1 inhibitor are administered concomitantly.

11. The method of claim 10, wherein the CCR2 chemokine receptor antagonist, and the PD-1 inhibitor and/or the PD-L1 inhibitor are administered in a combination formulation.

12. The method of claim 1, wherein the CCR2 chemokine receptor antagonist, and the PD-1 inhibitor and/or the PD-L1 inhibitor are administered sequentially.

13. The method of claim 12, wherein the CCR2 chemokine receptor antagonist is administered prior to administration of the PD-1 inhibitor and/or the PD-L1 inhibitor.

14. The method of claim 12, wherein the CCR2 chemokine receptor antagonist is administered after the administration of the PD-1 inhibitor and/or the PD-L1 inhibitor.

15. The method of claim 1, wherein the CCR2 chemokine receptor antagonist is administered orally and the PD-1 inhibitor and/or the PD-L1 inhibitor is administered intravenously.

16. The method of claim 1, wherein the mammal is a human subject.

* * * * *